United States Patent [19]
Hammock et al.

[11] Patent Number: 5,459,040
[45] Date of Patent: Oct. 17, 1995

[54] ENZYME AMPLIFIED, COMPLEX LINKED, COMPETITIVE AND NON-COMPETITIVE ASSAYS FOR THE DETECTION OF METAL IONS

[75] Inventors: Bruce D. Hammock; Ferenc Szurdoki; Horacio Kido, all of Davis, Calif.

[73] Assignee: The Regents of the University of California, Oakland, Calif.

[21] Appl. No.: 156,567

[22] Filed: Nov. 22, 1993

[51] Int. Cl.⁶ .............................. G01N 33/20; G01N 33; G01N 535; G01N 33/58
[52] U.S. Cl. .................... 435/7.1; 435/4; 436/56; 436/73; 436/77; 436/79; 436/80; 436/81; 436/83; 436/84; 436/501
[58] Field of Search ................. 435/7.1, 4; 436/73, 436/77, 79, 80, 81, 83, 84, 56, 501

[56] References Cited

U.S. PATENT DOCUMENTS

| | | | |
|---|---|---|---|
| 4,722,892 | 2/1988 | Meares et al. | 435/7 |
| 5,104,815 | 4/1992 | Garner et al. | 436/505 |
| 5,126,272 | 6/1992 | Kingston, Jr. et al. | 436/77 |
| 5,175,110 | 12/1992 | Bradshaw et al. | 436/77 |
| 5,244,816 | 9/1993 | Subramanian | 436/545 |
| 5,372,930 | 12/1994 | Colton et al. | 435/6 |

OTHER PUBLICATIONS

Vlatakis, G., et al., "Drug assay using antibody mimics made by molecular imprinting," Nature, vol. 361, pp. 645–647 (1993).
Wylie, D. E. et al., "Monoclonal antibodies specific for mercuric ions," Proc. Natl. Acad. Sci. USA, vol. 89, pp. 4104–4108 (1992).
Blanco, M., et al., "Simultaneous Spectrophotometric Determination of Zinc (II) and Nickel (II) with 1–(2–Pyridylazo)–2–Naphthol," Mikrochim. Acta, vol. 108, pp. 53–59 (1992).
Wylie, D. E., et al., "Detection of Mercuric Ions in Water by Elisa with a Mercury–Specific Antibody," Anal. Biochem., vol. 194, pp. 381–387 (1991).
Reardan, D. T., et al., "Antibodies against metal chelates," Nature, vol. 316, pp. 265–268 (1985).
Kamburova, M., "Spectrophotometric Determination of Mercury in Soils with Triphenyltetrazolium Chloride," Talanta, vol. 40, pp. 719–723 (1993).

Primary Examiner—David Saunders
Attorney, Agent, or Firm—Townsend and Townsend and Crew

[57] ABSTRACT

Methods of assaying for the presence or amount of a metal ion in a sample suspected of containing such ions. In one aspect, an enzyme amplified sandwich assay is provided which relies upon the ability of the analyte (metal ion) to form a complex with two complexing agents (chelators). In this assay, the first sandwich chelator is immobilized on a solid support, while the second sandwich chelator is linked to a reporter group (e.g., an enzyme). This assay combines the specific recognition of the analyte by the first and second sandwich chelators with the great signal amplification offered by the reporter group (e.g., enzyme). In another aspect, a competitive assay is provided that relies on the competitive inhibition of complex formation between the coating ligand (i.e., the chelator attached to the solid support) and the organometallic compound attached to the reporter group (e.g., enzyme) by the metal ions of interest present in the sample.

Using the methods of the present invention, hazardous metals, environmental pollutants, and other biomolecules can be selectively detected at ppb/ppt concentrations. More particularly, using the methods of the present invention, highly toxic metals (mercury, lead, cadmium, etc.) that pose serious human and environmental health hazards can be selectively detected at ppb/ppt concentrations. The methods of the present invention are particularly useful because they do not require the use of high affinity, highly specific antibodies which are expensive and difficult to produce.

31 Claims, 16 Drawing Sheets

OTHER PUBLICATIONS

Daniels, R. S., et al., "Cold–Vapor Mercury Atomic Absorption Spectometry I. Reagent volume Optimization," The Science of the Total Environment, vol. 89, pp. 319–323 (1989).

Guo, T., et al., "Determination of mercury in urine by flow–injection cold vapour atomic absorption spectrometry," Analytica Chimica Acta, vol. 278, pp. 189–196 (1993).

Lopez, E., et al., "Europium (III) Trisbipyridine Cryptate Label for Time–Resolved Fluorescence Detection of Polymerase Chain Reaction Products Fixed on a Solid Support," Clin. Chem., vol. 39, pp. 196–201 (1993).

Means, G. E., et al., "Reductive Alkylation of Amino Groups in Proteins," Biochem., vol. 7, pp. 2192–2201 (1968).

Böcher, M., et al., "Dextran, a hapten carrier in immunoassays for s–triazines: A comparison with Elisas based on hapten–protein conjugates," J. Immunol. Methods, vol. 151, pp. 1–8 (1992).

Nomura, M., et al., "A Pitfall in Two–Site Sandwich 'One–Step' Immunoassay with Monoclonal Antibodies for the Determination of Human Alpha–Fetoprotein," J. Immunol. Methods, vol. 56, pp. 13–17 (1983).

Lind, B., et al., "Mercury speciation in blood and brain tissue from monkeys. Interlaboratory comparison of Magos' method with other spectroscopic methods, using alkylation and gas chromatography separation as well as RNAA in combination with Westöö's extraction methods," Fresenius J. Anal. Chem., vol. 345, pp. 314–317 (1993).

Bond, A. M., et al., "Calculation of Thermodynamic Data from Voltammetry of Solid Lead and Mercury Dithiocarbamate Complexes Mechanically Attached to a Graphite Electrode," J. Phys. Chem., vol. 95, pp. 7460–7465 (1991).

Cabacungan, J. C., et al., "Amine Boranes as Alternative Reducing Agents for Reductive Alkylation of Proteins," Anal. Biochem., vol. 124, pp. 272–278 (1982).

Holmquist, B., "Elimination of Adventitious Metals," Methods Enzymol., vol. 158, pp. 6–12 (1988).

Stults, N. L., et al., "Immobilization of Proteins on Oxidized Crosslinked Sepharose Preparations by Reductive Amination," Anal. Biochem., vol. 180, pp. 114–119 (1989).

Tainturier, G., et al., "Electroassisted Glycosylation of Bovine Casein: An Alternative to the Use of Reducing Chemicals in N–Alkylation to the Use of Reducing Chemicals in N–Alkylation of Proteins," J. Agric. Food Chem., vol. 40, pp. 760–763 (1992).

Varenne, A., et al., "Transition Metal Carbonyl Labeling of Proteins. A Novel Approach to a Solid–Phase Two–Site Immunoassay Using Fourier Transform Infrared Spectroscopy," Bioconjugate Chem., vol. 3, pp. 471–476 (1992).

Khosravi, M. J., et al., "Hapten–Heterologous Conjugates Evaluated for Application to Free Thyroxine Immunoassays," Clin. Chem., vol. 39, pp. 256–262 (1993).

Wong, W. S. D., et al., "Pyridine Borane as a Reducing Agent for Proteins," Anal. Biochem., vol. 139, pp. 58–67 (1984).

Avrameas, S., "Amplification systems in immunoenzymatic techniques," J. Immunol. Methods, vol. 150, pp. 23–32 (1992).

Boguslaski, R. C. et al. (eds.), Clinical Immunochemistry: Principles of Methods and Applications, pp. 1–46, 157–168, 241–270, Little, Brown and Company (1984).

R = SOLID PHASE-BOUND PROTEIN OR REPORTER ENZYME

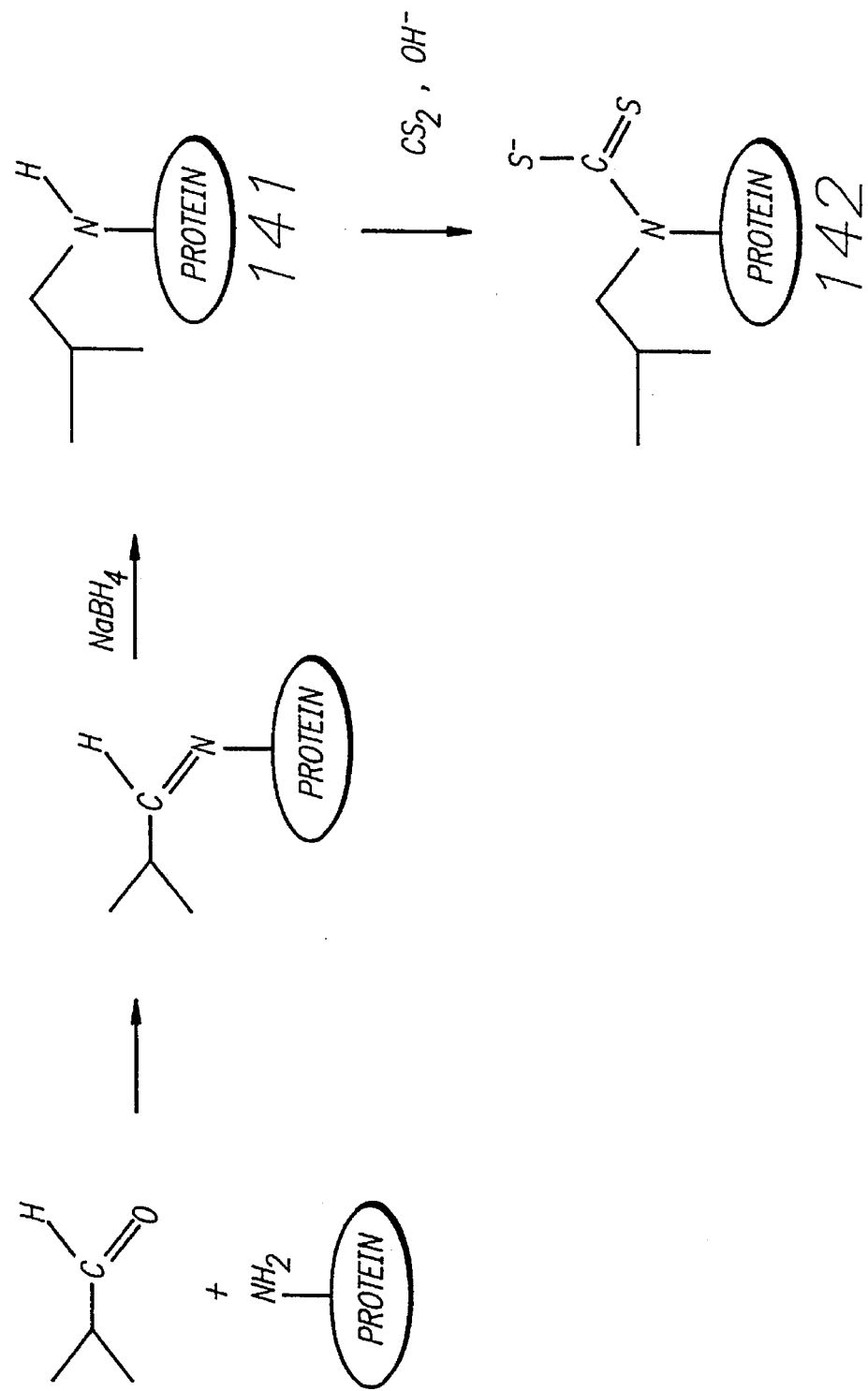
FIG. 6A SYNTHESIS OF 141 AND 142

SYNTHESIS OF 149, 152, AND 153

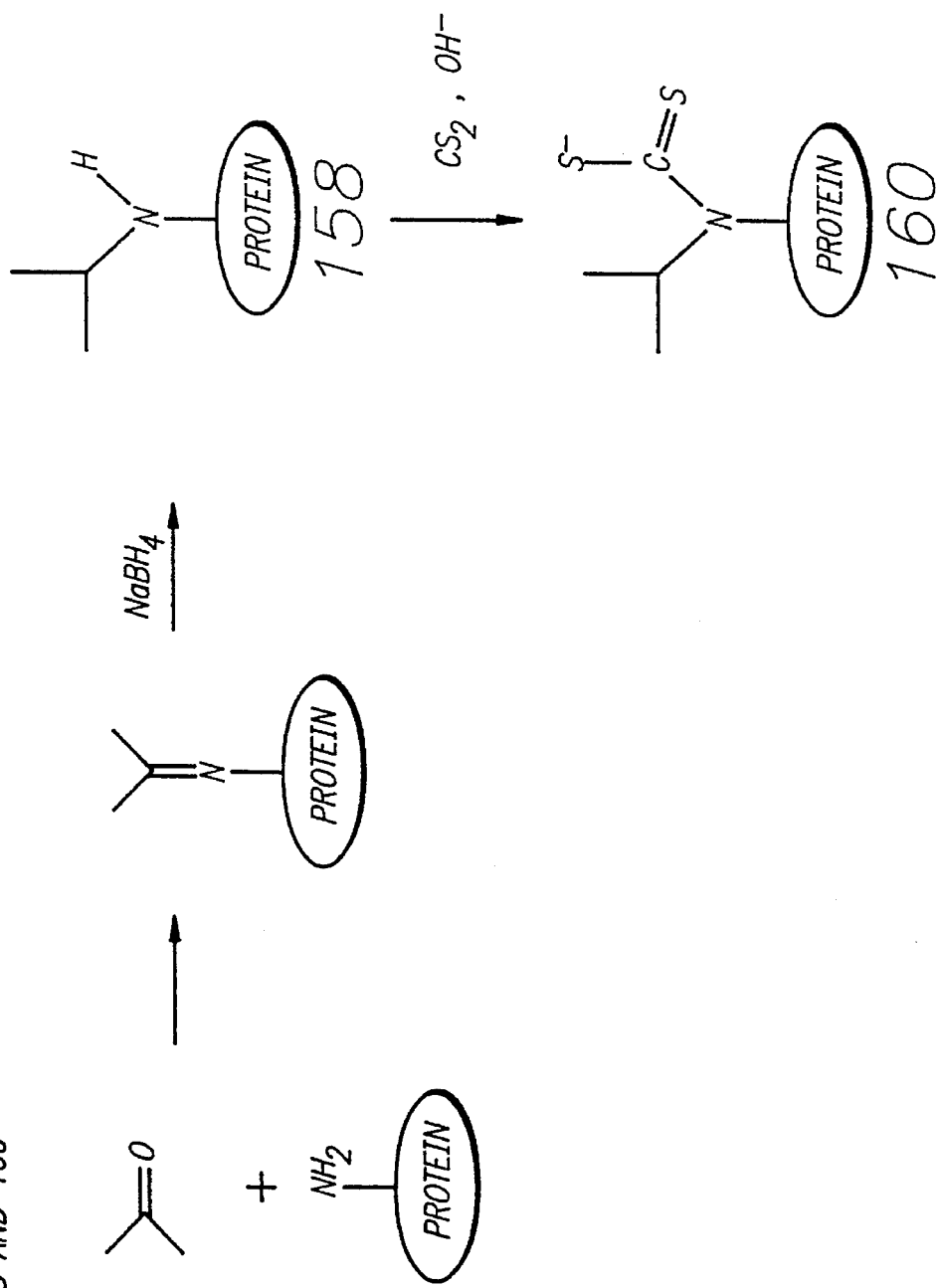
FIG. 7A SYNTHESIS OF 158 AND 160

SYNTHESIS OF 196

FIG. 8

| UNKNOWN SAMPLES | STANDARDS [Hg$^{++}$], nM |
|---|---|
| A | 3000 |
| B | 1000 |
| C | 300 |
| D | 100 |
| E | 30 |
| F | 10 |
| G | 3 |
| H | 1 |
| I | .3 |
| J | .1 |
| K | ZERO |
| L | BLANK |

FIG. 9

|  | | MERCURIC ION CONCENTRATION | | | | | | |
|---|---|---|---|---|---|---|---|---|
| FIRST SANDWICH CHELATOR | | 300 nM | 0 nM | 300 nM | 0 nM | 300 nM | 0 nM | 300 nM | 0 nM |
| CONCENTRATION A | | ▓ | | ▓ | | ▓ | | ▓ | |
| | | ▓ | | ▓ | | ▓ | | ▓ | |
| | | ▓ | | ▓ | | ▓ | | ▓ | |
| | | ▓ | | ▓ | | ▓ | | ▓ | |
| CONCENTRATION A | | ▓ | | ▓ | | ▓ | | ▓ | |
| | | ▓ | | ▓ | | ▓ | | ▓ | |
| | | ▓ | | ▓ | | ▓ | | ▓ | |
| | | ▓ | | ▓ | | ▓ | | ▓ | |
| CONCENTRATION A | | | | | | | | | |
| | | | | | | | | | |
| | | | | | | | | | |
| | | | | | | | | | |
| | CONCENTRATION 1 | | CONCENTRATION 2 | | CONCENTRATION 3 | | CONCENTRATION 4 | |

SECOND SANDWICH CHELATOR

ENZYME AMPLIFIED, COMPLEX LINKED, COMPETITIVE AND NON-COMPETITIVE ASSAYS FOR THE DETECTION OF METAL IONS

STATEMENT OF GOVERNMENT INTEREST

This invention was made with Government support under Grant No. P42 ES-04699, awarded by the National Institutes of Health. The Government has certain rights in this invention. This invention was also made with support from the University of California Systemwide Toxics Program.

FIELD OF THE INVENTION

In one aspect, the present invention relates to a method and kit for the detection and quantification of metal ions based on the use of an enzyme amplified sandwich chelate assay. In another aspect, the present invention relates to a competitive method for the detection and quantification of metal ions based on the use of an organometallic compound which competes with the metal ions present in the sample for the chelator. These methods are particularly well-suited for the detection and quantification of ions of various light, transition, heavy, lanthanide and actinide metals with various oxidation states. Such metal ions include, but not limited to, the following: antimony, arsenic, beryllium, cadmium, cerium, chromium, cobalt, copper (Cu(II)), gold, lead, manganese, mercury (Hg(II)), nickel, palladium, selenium, silver, thallium, uranium, zinc and zirconium. More particularly, the present invention relates to methods for the selective and quantitative detection of mercuric ions. Using the methods of the present invention, one can detect metal ions present in a sample at ppb/ppt concentrations.

BACKGROUND OF THE INVENTION

Mercury and most of its derivatives are extremely toxic substances which are ubiquitous in the biosphere. The major source of mercury contamination is the natural degassing of the earth's crust, although major contributions also arise from anthropogenic sources. The amount released from both sources do not cause problems on a global scale, but increases on a local level can lead to serious health problems with long-term consequences for the affected population. Thus, simple, sensitive and reliable procedures for the detection of mercury in the environment are needed.

Numerous approaches for detecting transition/heavy metals with sensitivity in the parts per million (ppm)/high parts per billion (ppb) range can be found in the literature (see, e.g., Blanco, M., et al., *Mikrochira. Acta*, 108: 53–59 (1992)). These approaches are primarily based on the detection of suitable metal derivatives by molecular absorption spectrophotometry (e.g., UV-VIS, IR) or by electroanalytical techniques. Many of these techniques employ the use of chelates derived from the metal ions present in the sample being analyzed. Metal ions in complex matrices have also been measured in the form of chelates by both gas chromatography (GC) and liquid chromatography (LC).

Simple mercury analyses based on the detection of chelates using optical techniques (such as, for example, UV-VIS photometry) often suffer from interferences by foreign ions (see, Sharma, R., et at., *Talanta*, 36: 457–461 (1989)), and they usually lack the necessary high sensitivity (see, Madseal, M., *J. Anal. Chem.*, 342: 157–162 (1992); and Kamburova, M., *Talanta* 40(5): 719–723 (1993). This is true despite the fact that these methods are frequently combined with chelate extraction techniques (e.g., preconcentration techniques). Only occasionally have detection limits below 0.1 ppm been reported in the literature (see, Mariscal, M., et al., ibid.).

As such, relatively few simple, reliable, and selective techniques are available for the detection of transition/heavy metals at parts per billion (ppb)/parts per trillion (ppt) levels. The most commonly used methods involve instrumental analyses, such as, for example, flameless atom absorption spectroscopy, inductively coupled plasma mass spectrophotometry, special electroanalytical methods, etc. (See, Daniels, R., et al., *Sci. Total Environ.*, 89: 319–339 (1989).) These methods, however, possess many of the limitations that are typically encountered when using instrumental analyses: the sample throughput is limited; they cannot process multiple samples in parallel; and they are not suitable or amendable to on-site analysis in the field (see, Wylie, D., et al., *Anal. Biochem.*, 194: 381–387 (1991)).

Interesting alternative methods involve immunoassay procedures for the detection of certain lanthanida elements and heavy metals (see, Reardan, et al., *Nature*, 316: 265–268 (1985); Wylie, D., et al., ibid., (1991); Wylie, D., et al., *Proc. Natl. Acad. Sci. USA*, 89: 4104–4108 (1992)). In these methods, antibodies are raised against metal chelates. Reardan, et al. succeeded in the recognition of an EDTA-type of chelate of indium by monoclonal antibodies generated by the same chelate attached to a carrier protein. The antibodies displayed the highest affinity to the indium-chelate; however, chelates of various heavy metal ions had affinities of only 10–1000 times less than the indium-chelate. This lack of selectivity can create significant difficulties if real samples containing other metal ions in moderate to high concentrations were to be analyzed using this method. Moreover, Wylie, et al., ibid., immunized mice with $HgCl_2$-glutathione-KLH. Some of the monoclonal antibodies that were obtained selectively recognized the mercuric ions either chelated to glutathione-BSA or alone. One of the resulting ELISAs, based on the use of the most effective antibodies, showed a linear relationship between the optical density and $\log[Hg^{2+}]$ in the range of 0.5–10 ppb. Although these method exhibit some degree of specificity, they both have significant limitations in that they require the use of highly specific monoclonal antibodies that are difficult and expensive to prepare.

As such, in environmental and clinical laboratories, the most routinely used method for the determination of mercury is cold-vapor atomic absorption spectrometry (i.e., CVAAS). (See, Magos, L., et at., *J. Assoc. Of Anal. Chem.*, 55: 966–971 (1972); Lind, et al., Fresenius *J. Anal. Chem.* 345: 314–317 (1993); Guo, T., et al., *J. Anal. Chim. Acta.*, 278: 189–196 (1993)). However, this technique also has a number of limitations. As with the other methods involving instrumental analyses, the number of samples that can be analyzed is limited by the fact that only one sample can be analyzed at a time. Additionally, a large sample volume (i.e., up to 5 mL) is required to ensure maximum sensitivity, although assays performed at maximum sensitivity often lack high precision. Moreover, CVAAS requires the use of expensive equipment and highly skilled personnel, and it is not suitable or amendable to on-site analysis in the field (see, Wylie, et al., ibid. (1991)).

In the case of mercury, chemical speciation (i.e., inorganic versus organic mercury) is of utmost toxicological importance. Of particular interest is methylmercury. Methylmercury, produced by bacterial methylation of Hg(II) in aquatic sediments, is by far the most toxic and most commonly occurring organic mercury species (see, Palmisano, F., et al.,

*J. Anal. Chem.*, 346: 648–652 (1993)). It is significantly more toxic than Hg(II), i.e., inorganic mercury. Methylmercury accumulates in fish and is amplified through the food chain; thus, its concentration in natural waters is one of the most important water quality parameters (see, Bloom, N., et al., *Water Air Soil Pollut.*, 53: 251–265 (1990)). The abundance and the toxicological significance of Hg(0) and Hg(I) in aquatic environments is only marginal. The CVAAS technique detects the amount of Hg(II), i.e., inorganic mercury. However, the quantification of organic mercury (i.e., total mercury-inorganic mercury) is possible indirectly by decomposition of the organic species into Hg(II) and then by the determination of the total mercury content (see, Magos, L., ibid.; Lind, et al., ibid.; Guo, T., et al., ibid.). Other common methods for determining mercury speciation combine chromatographical separation of the mercury derivatives using various detection systems (see, Bulska, E., et al., *Analyst*, 117: 657–663 (1992); Palmisano, F., et al., ibid.; Lind, et al., ibid.). However, all of these methods require the use of costly apparatuses and highly qualified analysts. Moreover, the analysis rate is limited because only one sample can be measured at a time.

As such, there still exists a need for a simple, sensitive and reliable methods for the detection of mercury and other metal ions in environmental and biological samples. The present invention remedies this need by providing such methods.

SUMMARY OF THE INVENTION

The present invention provides rapid, accurate and selective methods and kits for the detection and quantification of a metal ion in a sample suspected of containing such metal ions. More particularly, the present invention relates to methods and kits for detecting the presence and/or quantity of ions of various light, transition, heavy, lanthanide and actinide metals with various oxidation states. Such metal ions include, but not limited to, the following: antimony, arsenic, beryllium, cadmium, cerium, chromium, cobalt, copper (Cu(II)), gold, lead, manganese, mercury (Hg(II)), nickel, palladium, selenium, silver, thallium, uranium, zinc and zirconium.

In one aspect, the present invention provides a method for assaying for the presence and, when desired, the quantity of a metal ion in a sample suspected of containing the metal ion, the method comprising: (a) contacting the sample with a solid support, the solid support having a first sandwich chelator immobilized thereon in a manner such that the first sandwich chelator is capable of binding with the metal ion to form a chelate complex; (b) contacting the sample with a second sandwich chelator, the second sandwich chelator having a reporter group immobilized thereon in a manner such that the second sandwich chelator is capable of binding with the chelate complex to form a sandwich chelate complex; and (c) detecting the presence of the sandwich chelate complex by the presence or absence of the reporter group.

This particular method relies upon the ability of the analyte (i.e., metal ion) to form an aggregate or complex with two complexing agents, i.e., chelators. Such an association is termed a sandwich complex with the analyte or target compound forming the middle of the sandwich. In this method, one of the complexing agents (i.e., the first sandwich chelator) is immobilized on a solid support, while the other complexing agent (i.e., the second sandwich chelator) is linked or bound to a reporter group (e.g., an enzyme). This arrangement forms a highly selective, sensitive, and convenient system for the quantitative detection of the target analyte. This approach combines the specific recognition of the target compounds by the sandwich complexing agents, i.e., the first and second sandwich chelators, with the great signal amplification offered by enzymes or other appropriate reporting groups or systems. With the application of this method, there is no need for high affinity, highly specific antibodies which are expensive and difficult to produce. Moreover, this method does not require the use of expensive equipment and highly skilled personnel, and it is suitable and amendable to on-site analysis in the field.

In another aspect, the present invention provides a competitive method for assaying for the presence of a metal ion in a sample suspected of containing the metal ion, the method comprises: (a) contacting the sample with a solid support, the solid support having a chelator immobilized thereon in a manner such that the chelator is capable of binding with the metal ion to form a chelate complex; (b) adding to the sample an organometallic compound that is capable of binding with the chelator to form a chelate complex, the organometallic compound having immobilized thereon a reporter group; and (c) detecting the presence of the metal ion through the presence or absence of the reporter group.

This competitive assay format relies on the competitive inhibition of complex formation between the coating ligand (i.e., the chelator attached to the solid support) and the organometallic compound attached to the reporter group or system (e.g., enzyme) by the metal ions of interest present in the sample. Since the amount of organometallic compound that is bound to the chelator will be inversely proportional to the quantity of metal ion present in the sample, the optical density response will also be inversely proportional to the quantity of metal ion present. A standard curve such as the one in FIG. 10 can be generated. Samples containing unknown concentrations of metal can be evaluated and the concentration of the metal ion determined by diluting them so that their corresponding optical density responses fall within the standard curve's linear range. Using this competitive assay format, one can detect metal ions at ppb/ppt concentrations. As with the enzyme amplified sandwich assay, this method does not require the need for high affinity, highly specific antibodies which are expensive and difficult to produce. Moreover, as with the enzyme amplified sandwich assay, this method does not require the use of expensive equipment and highly skilled personnel, and it is suitable and amendable to on-site analysis in the field.

The methods of the present invention are well-suited for the selective detection of hazardous metals, environmental pollutants, and other biomolecules present at very low levels, i.e., at ppb/ppt concentrations. Moreover, the methods of the present invention are particularly well-suited for the environmental monitoring of certain highly toxic metals (mercury, lead, cadmium, etc.) that pose serious human and environmental health hazards and that are frequently present at very low levels, i.e., at ppb/ppt concentrations.

BRIEF DESCRIPTION OF THE DRAWINGS

FIGS. 6A and 6B sets forth the reaction scheme used to prepare the dithiocarbamate chelator #142 (FIG. 6A) and the dithiocarbamate chelator #153 (FIG. 6B).

FIGS. 7A and 7B sets forth the reaction scheme used to prepare the dithiocarbamate chelator #160 (FIG. 7A) and the organomercuric compound #196 used in the competitive assay format (FIG. 7B).

FIG. 8 sets forth the plate format for determining Hg(II) in unknown samples.

FIG. 9 sets forth the two dimensional titration scheme for sandwich chelators on 96-well microtiter plate (quadruplicate samples).

DETAILED DESCRIPTION OF THE INVENTION AND PREFERRED EMBODIMENTS

Figure 1:
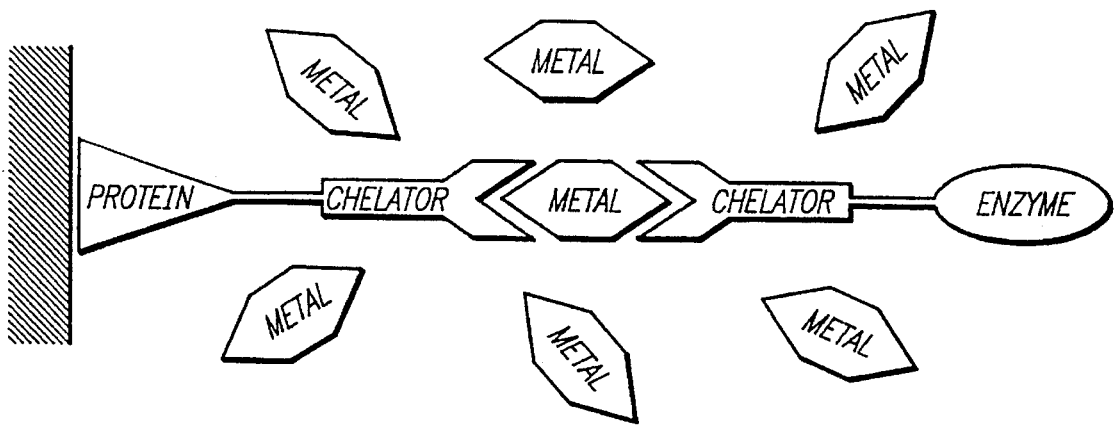
FIG. 1 sets forth the general principle of the enzyme amplified sandwich complex assay used in a method of the present invention.

In one aspect, the present invention provides a method for assaying for the presence of a metal ion in a sample suspected of containing the metal ion, the method comprising: (a) contacting the sample with a solid support, the solid support having a first sandwich chelator immobilized thereon in a manner such that the first sandwich chelator is capable of binding with the metal ion to form a chelate complex; (b) contacting the sample with a second sandwich chelator, the second sandwich chelator having a reporter group immobilized thereon in a manner such that the second sandwich chelator is capable of binding with the chelate complex to form a sandwich chelate complex; and (c) detecting the presence of the sandwich chelate complex by the presence or absence of the reporter group. (See, FIG. 1.)

This method of the present invention can be used to selectively detect and, where desired, quantitate metal ions present in a sample. More particularly, the present invention can be used to selectively detect ions of light, transition, heavy, lanthanide and actinide metals with various oxidation states. Such metal ions include, but are not limited to, the following: antimony, arsenic, beryllium, cadmium, cerium, chromium, cobalt, copper (Cu(II)), gold, lead, manganese, mercury (Hg (II)), nickel, palladium, selenium, silver, thallium, uranium, zinc and zirconium. As used herein, the term "sample" refers to any sample derived from a biological (e.g., serum, urine), environmental (e.g., ground water, ponds, lakes, rivers, oceans), industrial (e.g., chemical manufacturing operations) or commercial (e.g., food products) source that is suspected of containing the metal ions of interest. Moreover, as used herein, the term "contacting" can be used interchangeably with the following: combined with, added to, mixed with, passed over, flowed over, etc.

The terms first and second sandwich chelators, as used herein, refer to compounds that are capable of forming a complex or (interchangeably) a coordination compound with the analyte (i.e., metal ion) being detected. The chelator employed in this method of the present invention must be capable of selectively detecting the analyte of interest, and it must be capable of forming a thermodynamically stable sandwich chelate complex (i.e., a chelator-analyte-chelator complex). Examples of suitable first and second sandwich chelators include, but are not limited to, the following: dithiocarbamates, 2,3-dimercaptopropanesulphonic acid, 2,3-dimercaptopropanol-1, D,L-penicillamine, 2-(3-sulfobenzoyl)pyridine-2-pyridylhydrazone, selenohydryl-containing compounds, 4-(2-pyridylazo)resorcinol, diphenylthiocarbazone, 1-(2-pyridylazo)-2-naphthol, 6-amino-1-naphthol-3-sulphonic acid, histidine and acetylacetone.

The particular chelators used in this method of the present invention will depend on which metal ion is being detected, and the selection in any given case will be apparent to those of skill in the art. For example, if mercury (Hg(II)) is to be detected, the following chelators can be used: dithiocarbamates (see, Bond, A. M. and Scholz, F., *J. Phys. Chem.*, 95: 7460–7465 (1991)); 2,3-dimercaptopropanesulphonic acid (i.e., unithiol) (see, Casas, J. S., et al., *J. Inorg. Nucl. Chem.*, 42: 99–102 (1980)); 2,3-dimercaptopropanol-1 (see, Casas, J. S., et al., ibid. (1980)); D,L-penicillamine (see, Casas, J. S., et al., ibid. (1980)); 2-(3-sulfobenzoyl)pyridine-2-pyridyl-hydrazone (see, Going and Sykora, *Anal. Chim. Acta*, 70: 127–132 (1974)); and selenohydryl-containing compounds (see, Arnold, A. P., et al., *Inorg. Chem.*, 25: 2433–2437 (1986)). For the detection of thallium, the following chelator can be used: 4-(2-pyridylazo)resorcinol (see, Hnilicková, et al., *Talanta*, 16: 83–94 (1986)). If cobalt is to be detected, the following chelator can be used: 4-(2-pyridylazo)resorcinol (see, Yotsuyanagi, T., et al., *Anal. Chem.*, 44: 1091–1093 (1972)). For the detection of lead, the following chelator can be used: diphenyl-thiocarbazone (i.e., dithizone) (see, Budesinsky and Sagat, *Talanta*, 20: 228–232 (1973)). If uranium is being detected, the following chelator can be used: 1-(2-pyridylazo)-2-naphthol (i.e., PAN) (see, Cheng, K. L., *Anal. Chem.*, 30: 1027–1030 (1958)). For the detection of selenium, the following chelator can be used: 6-amino-1-naphthol-3-sulphonic acid (i.e., J-acid) (see, Ramachandran, K. N., et al., *Talanta*, 40: 781–784 (1993)). If copper (Cu(II)) is being detected, the following chelator can be used: histidine (see, Meyer and Bauman, *J. Amer. Chem. Soc.*, 92: 4210–4216 (1970)). For the detection of beryllium, the following chelator can be used: acetylacetone (see, Aller, A. J., *Appl. Spectr.*, 44: 1159–1162 (1990)). Such chelators are prepared using standard methods and techniques known to those of skill in the art. (See, e.g., the Example Section, infra). All of the foregoing publications are hereby incorporated by reference in their entirety.

It will be readily apparent to those of skill in the art that this method of the present invention is not limited to the use of the foregoing chelators. To be useful in this method of the present invention, the chelator must be capable of selectively detecting the analyte of interest, and it must be capable of forming a sandwich chelate complex (i.e., a chelator-analyte-chelator complex). As such, any complexing agent (i.e., those presently known or those developed in the future) that is capable of selectively forming sandwich chelates of high thermodynamic stability with the target analyte under appropriate kinetics (i.e., fast rate of formation relative to analysis time) can be used to carry out the detection method of the present invention. It will be understood by those of skill in the art that routine kinetics experiments can be used to determine the rate of formation of the sandwich chelate complex. Moreover, the conditional stability constant $\beta_2$, which is a direct measure of a sandwich chelate complex's thermodynamic stability, can be measured through the use of numerous methods known to those of skill in the art. These methods are primarily based on the preparation of a series of solutions containing known amounts of the complex forming components, and the monitoring of the concentration (i.e., the formation or depletion) of one of the reactants or products, either directly or indirectly, using a suitable analytical method. Such analytical methods are known to those of skill in the art and include, for example, potentiometric, spectrophotometric, polarographic, extraction and ion exchange methods.

For the evaluation of the conditional stability of water-insoluble sandwich chelate complexes, such as those formed by dithiocarbamates, a cyclic voltammetry method (i.e., a type of polarography) that involves the mechanical attachment of the sandwich chelate complex onto a paraffin impregnated graphite electrode can be used. (See, Bond, A. M. and Scholz, F., ibid. (1991), which is incorporated herein by reference.) The electrode with the attached sandwich chelate complex is immersed into an electrolyte solution and an electrical potential is applied to the system. The sandwich chelate complex is subsequently reduced, liberating the water-soluble dithiocarbamate (which dissolves into the electrolyte solution), and the reduced metal (which remains on the electrode). By measuring the formal potential for this reaction, it is possible to calculate $\beta_2$ through the use of common electrochemical principles. It will be readily apparent to those skilled in the art that this particular method and other methods similar in principle to this method can be used to calculate the thermodynamic stability of the sandwich chelate complex.

It will be further understood by those of skill in the art that the pH of the buffer, the ionic strength of the buffer, the presence of a masking agent (i.e., extra chelating reagent added to the system to decrease interferences with foreign ions), etc., can influence the selectivity of the sandwich assay. For example, the same chelator can form useful systems with different metal ions depending upon the reaction conditions employed in the assay (e.g., 4-(2-pyridylazo)resorcinol can be used as a chelator for the detection of either thallium or cobalt). Moreover, in some instances, a simple cleanup of the sample (e.g., chelate extraction) can be advantageously used to improve and enhance the selectivity of the assay (e.g., beryllium/acetylacetone system). By running routine titration experiments, such as those set forth herein below, one of skill in the art can optimize the reaction conditions for the particular chelator being used and the particular metal ion being detected.

In this method of the present invention, the first sandwich chelator is immobilized on or bound to a solid support or solid phase (i.e., an insoluble polymeric material, inorganic or organic matrix, gel, aggregate, precipitate or resin) in a manner such that it is capable of binding with the metal complex to form a chelate complex, i.e., a first sandwich chelate-metal ion complex. Preferred solid supports in accordance with the present invention include, but are not limited to, the following: cellulose, agarose, dextran, polyacrylate, polyacrylamide, polystyrene, polyvinyl chloride, or their derivatives, chitin, sepharose, oxirane substituted acrylic beads, starch, oxidized starch (i.e., polymeric dialdehyde), collagen, keratin, elastin, bovine hide powder, bacterial cell wall peptidoglycan or fragments thereof, diazotized paper, nylon, polyethylene terephthalates, polycarbonates, metallic particles and controlled pore glass. Of these, certain solid supports are presently preferred, namely, cellulose and cellulose derivatives (e.g., nitrocellulose), agarose, dextran, polyacrylate, polyacrylamide, polystyrene, polyvinyl chloride and glass. Even more preferred for use as a solid support are nitrocellulose, polystyrene and polyvinyl chloride. Polystyrene and polyvinyl chloride are normally used as microtiter plates, while nitrocellulose is normally used in sheets.

Immobilization of the first sandwich chelator onto the solid support is carded out using conventional methods and procedures known to and understood by those skilled in the art. Frequently, the first sandwich chelator is immobilized on the solid support through the use of a cross-linking reagent and, if necessary, a linker molecule or (interchangeably) a spacer molecule. Cross-linking reagents are well known and a considerable range of such reagents is available commercially. In general, a cross-linking reagent comprises two or more reactive functional groups covalently linked together. The covalent linkage may be direct, but in many cases the reactive functional groups are spaced apart by respective covalent attachment to a spacer linkage. The reactive functional groups may be the same (i.e., a homofunctional cross-linking agent) or, they may be different (i.e., a heterofunctional cross-linking agent).

Suitable cross-linking reagents in accordance with the present invention include, but are not limited to, the following: S-acetylthioglycolic acid N-hydroxysuccinimide ester; N-(5-azido-2-nitrobenzyloxy)succinimide; p-azidophenacyl bromide; N-(4-azidophenylthio)phthalimide; 4-azidosalicylic acid N-hydroxysuccinimide ester; bromoacetic acid N-hydroxysuccinimide ester; 1,4-butanediol diglycidyl ether; 2-diazo-3,3,3-trifluoropropionic acid p-nitrophenyl ester; dimethyl adipimidate dihydrochloride; dimethyl 3,3'-dithiobispropionimidate dihydrochloride; dimethyl pimelimidate dihydrochloride; dithiobis(propionic acid N-hydroxysuccinimide ester); ethylene glycol bis-(succinic acid N-hydroxysuccinimide ester); 4-fluoro-3-nitrophenyl azide; bis(4-fluoro-3-nitrophenyl)sulfone; 4-(N-maleimido)benzophenone; γ-maleimidobutyric acid N-hydroxysuccinimide ester; ε-maleimidocaproic acid N-hydroxysuccinimide ester; 4-(N-maleimidomethyl)cyclohexane-1-carboxylic acid N-hydroxysuccinimide ester; β-maleimidopropionic acid N-hydroxysuccinimide ester; N,N'-bis(3-maleimidopropionyl)-2-hydroxy-1,3-propanediamine; N,N'-o-phenylene dimaleimide; polyoxyethylene bis(glycidyl ether); polyoxyethylene bis(imidazolyl carbonyl); and suberic acid bis(N-hydroxysuccinimide) ester, etc.

Moreover, suitable linker molecules in accordance with the present invention include, but are not limited to, the following: proteins, carbohydrates, lipids, peptides, polyesters, nucleic acids and synthetic polymers (e.g., poly-L-lysine) (See, e.g., Aoutsuka, S., et al., *J. Immunol. Methods*, 28:149–162 (1979); Presentini, R., et al., *J. Immunoassay*, 10:395–412 (1989); and Verschoor, J. A., et al., *J. Immunol. Methods*, 127: 43–49 (1990), the disclosure of which are incorporated herein by reference). The linker molecule can be bifunctional (i.e., it may have two reactive sites) wherein one of the reactive sites is used for attachment to the solid support, while the other reactive site is used to attach the chelator. Generally, the first sandwich chelator can be attached to the linker molecule and, in turn, the solid support using a cross-linking reagent, supra, in a Schiff base formation reaction with an aldehyde group; an amide formation reaction with an amine or carboxylic acid group using a peptide coupling reagent (such as, for example, carbodiimide, acid chloride and the like, supra); an ester formation reaction with a hydroxyl or carboxylic acid group using condensing agents; a sulfide formation reaction using a sulfide coupling agent, supra; an azo bond formation reaction with an aromatic diazonium salt; or other known coupling reactions for joining organic molecules to proteins. See, reviews of such methods and techniques: e.g., Kabat, E. A., *Structural Concepts In Immunology and Immunochemistry* (2nd Ed., Holt, Rinehart and Winston, New York (1976)); Eyzaguirre, J., *Chemical Modifications of Enzymes: Active Site Studies* (John Wiley & Sons (1982)); Wong, S. S., *Chemistry of Protein Conjugation and Cross-Linking* (CRC Press, Inc., Boca Raton, 1991); and Brinkley, M., *Bioconjugate Chem.*, 3: 2–13 (1992), the disclosures of which are incorporated herein by reference.

It will further be understood by those of skill in the art that an alternative to the use of bifunctional agents for immobilization is the application of commercially available, special microtiter plates with linker groups attached to the surface of the plates. These linkers make possible direct covalent coupling of the first sandwich chelator to the microtiter plates (see, e.g., Roch, A. M., et al., *J. Immunol. Methods*, 133: 1–11 (1990); and Sondergård-Andersen, J., et al., *J. Immunol. Methods*, 131: 99–104 (1990), the disclosures of which are incorporated herein by reference). Another alternative to the use of a cross-linking reagent for immobilization is to employ a speical first sandwich chelator (e.g., a compound having a chelating moiety attached to a linker group or molecule) which is capable of direct coupling to the spacer molecule or to the solid support.

In a presently preferred embodiment, proteins are the linker molecules used to attach the first sandwich chelator to the solid support. Such proteins include, but are not limited to, the following: bovine serum albumin, conalbumin, keyhole limpet hemocyanin and ovalbumin. Moreover, in a further preferred embodiment of the present invention, the first sandwich chelator linked to a protein (e.g., BSA, CONA, KLA, OVA, etc.) is doped on the surface of a polystyrene or polyvinyl chloride microtiter plate (i.e., an ELISA plate) using the methodology applied in the immunoassay field for coating microtiter plates. It will be readily apparent to those of skill in the art, however, that other methods can be used to attach the first sandwich chelator to the solid phase or support. As such, the mode of attaching the first sandwich chelator to the linker molecule and, in turn, the solid support is not a critical feature of the present invention.

The second sandwich chelator has a reporter group or (interchangeably) a reporter system immobilized thereon or linked thereto in a manner such that the second sandwich chelator is capable of binding with the chelate complex (i.e., the first sandwich chelate-metal ion complex) to form a sandwich chelate complex. As used herein, the term "reporter group" refers to any moiety, molecule, atom or species that results in a detectable signal or change when the analyte of interest (e.g., metal ion) is present in the sample. The reporter group can, itself, be a detectable signal (i.e., a detectable label, e.g., $^{125}$I) or, alternatively, the reporter group can be capable of undergoing a detectable change or of bringing about a detectable change. The presence of the detectable signal or change is an indication that the analyte of interest is present in the sample or specimen.

In accordance with the present invention, suitable reporter groups include, but are not limited to, the following: enzymes, chromogens, fluorophores, radioisotopes and biotin, or to these groups attached to an antibody that recognizes the sandwich chelate. In a presently preferred embodiment of the present invention, enzymes are used as the reporter group. When an enzyme is used as the reporter group, it is used in combination with an indicator, i.e., a chemical species or substrate which undergoes a detectable change as a result of the reaction or, as a result of the culmination of reactions occurring when the enzyme is present in the sample. Preferred indicators are visual indicators and, in particular, chromogenic indicators, i.e., those in which the visible change is a change in color, including the formation of color in an otherwise colorless material, upon action of the enzyme. Alternatively, the enzyme may be capable of catalyzing the formation of a fluorescent signal, a phosphorescent signal, a bioluminescent signal, a chemiluminescent signal, or an electrochemical signal. Additionally, the enzyme may be capable of producing other visible or detectable signals, such as, for example, a clot, an agglutination, a precipitation, or a clearing zone. In these cases, the indicator would be the chemical species or substrate required by the enzyme in order to bring about the desired detectable signal or change.

In accordance with the present invention, presently preferred enzymes for use as reporter groups include, but are not limited to, the following: horseradish peroxidase (HRP) and alkaline phosphatase (AP). A wide variety of chromogenic substrates (i.e., chromogens) can be employed when horseradish peroxidase and alkaline phosphatase are used as reporter groups. Suitable chromogens for HRP include, but are not limited to, the following: tetramethylbenzidine (TMB), chloronaphthol, aminoethylcarbazole and diaminobenzidine. Suitable chromogens for AP include, but are not limited to, the following: p-nitrophenyl phosphate (NPP) and bromochloroindolyl phosphate-nitro blue tetrazolium (BCIP/NBT). It will be apparent to those of skill in the art that the use of other enzymes as reporter groups is possible provided such enzymes can be linked or bound to the appropriate chelator and are capable of catalyzing a reaction which produces a detectable change, e.g., a color change. Additionally, the most appropriate chromogenic substrate for any given enzyme will depend upon the reaction or reactions which the enzyme is capable of catalyzing or initiating, and the selection in any given case will be readily apparent to those skilled in the art.

Moreover, as previously mentioned, the second sandwich chelator can be linked to or labeled with radioactive compounds (e.g., $^{125}$I), biotin, fluorophores, etc. Iodine-labeled reporter groups can be detected either by autoradiography or by direct counting in a gamma-counter. Biotin-labeled reporter groups are detected by using avidin or streptavidin. These proteins bind tightly to biotin, forming an essentially irreversible complex. Both avidin and streptavidin can be labeled with iodine or enzymes, and both are available commercially. Additionally, any other compounds which produce, either directly or indirectly, UV-VIS absorbance, fluorescence, fluorescence polarization, luminescence, IR, electron spin resonance spectroscopies, nonenzymatic catalysis (e.g., synthetic enzyme models), or any other specific effects (e.g., spectral, electrochemical, etc.) can be used as reporter groups in this method of the present invention. It is also conceivable that the sandwich chelate complex formed with the target metal ion may, itself, exhibit some chemical or physical characteristics (e.g., catalytic or spectral properties) which directly make possible the detection of the chelate.

It will be understood by those of skill in the art that the second sandwich chelator is immobilized on (i.e., linked or bound to) the reporter group or reporter system using methodology similar to that set forth for linking the first sandwich chelator to the solid support. As such, the previous discussion pertaining to the use of cross-linking agents to link organic molecules (i.e., chelators) to proteins and other molecules is fully applicable here. Using the cross-linking reagents set forth above, one of ordinary skill in the art can readily link the second sandwich chelator to the reporter group or reporter system using conventional coupling reactions known to those in the art. An alternative to the use of a cross-linking reagent for immobilization is to employ a special second sandwich chelator (e.g., a compound having a chelating moiety attached to a linker group) which is capable of direct coupling to the reporter system.

Figure 2:
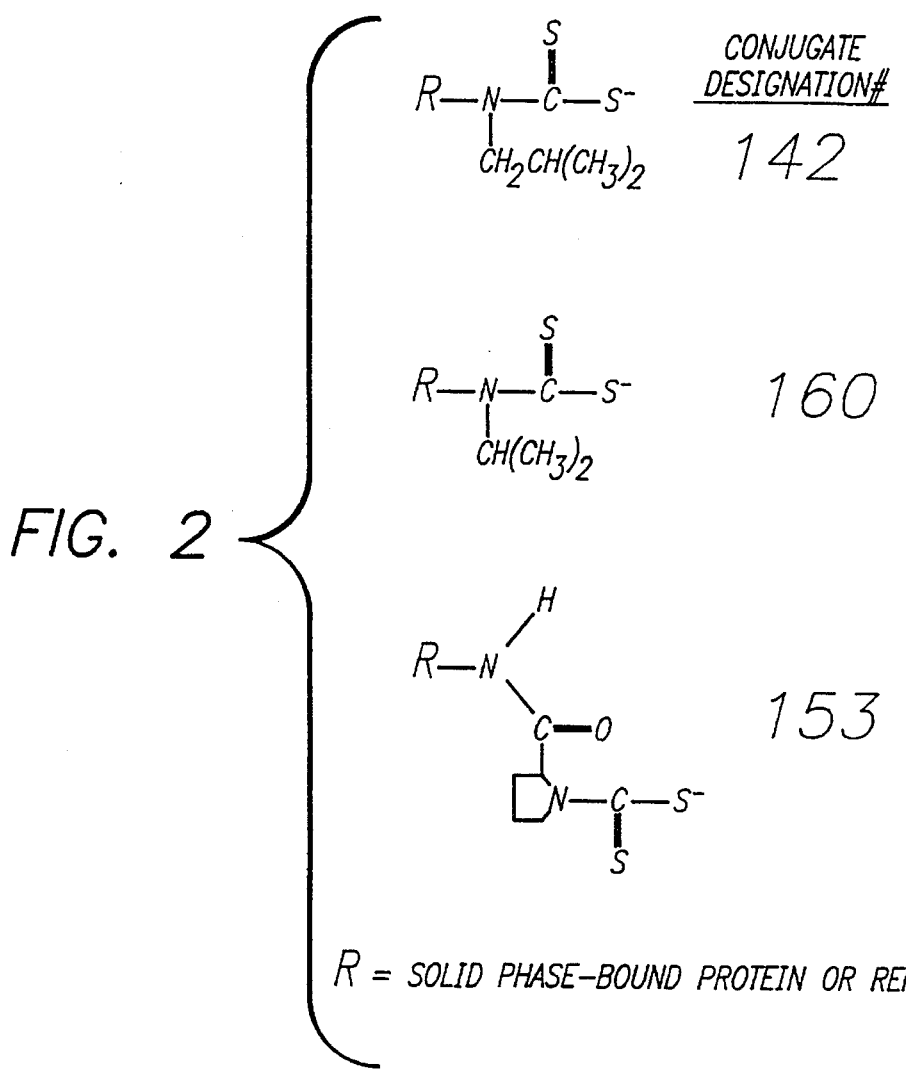
FIG. 2 sets forth the structures of the dithiocarbamate containing conjugates used in the methods of the present invention.

In a presently preferred embodiment, mercuric ions are the metal ions that are quantitatively detected in this method of the present invention. Dithiocarbamates are employed as the chelators in this particular method of the present invention as these compounds have very high affinities for certain heavy metal ions and, in particular, for mercury(II) ions. The chemical reactions used to prepare both the first sandwich chelator (i.e., a dithiocarbamate chelator linked to a protein) and the second sandwich chelator (i.e., the enzyme linked to a dithiocarbamate chelator) are very similar. Briefly, secondary amino groups are generated by routine procedures on the surface of the macromolecules (i.e., proteins and enzymes), then carbon disulfide is added to obtain the corresponding dithiocarbamates (FIG. 2). (See, the Example Section, infra, for a more detailed description of the procedures used to prepare the dithiocarbamate chelators that are useful in this method of the present invention.) Dithiocarbamates obtained from secondary amines are known to be fairly stable under nonacidic conditions in the absence of oxidizing agents. Primary amines are not particularly useful as chelators in this method because they form chemically unstable dithiocarbamates leading to extensive cross-linking of the proteins and enzymes used in the assay (see, Valentine, W., et al., *Chem. Res. Toxicol*, 5:254–262 (1992) which is incorporated herein by reference). Once formed, the first sandwich chelator, i.e., a dithiocarbamate chelator linked to a protein (e.g., BSA, CONA, KLH, OVA), can be conveniently doped on the surface of the ELISA plates making use of the methodology applied commonly in the immunoassay field for coating the microtiter plates.

Figure 3:
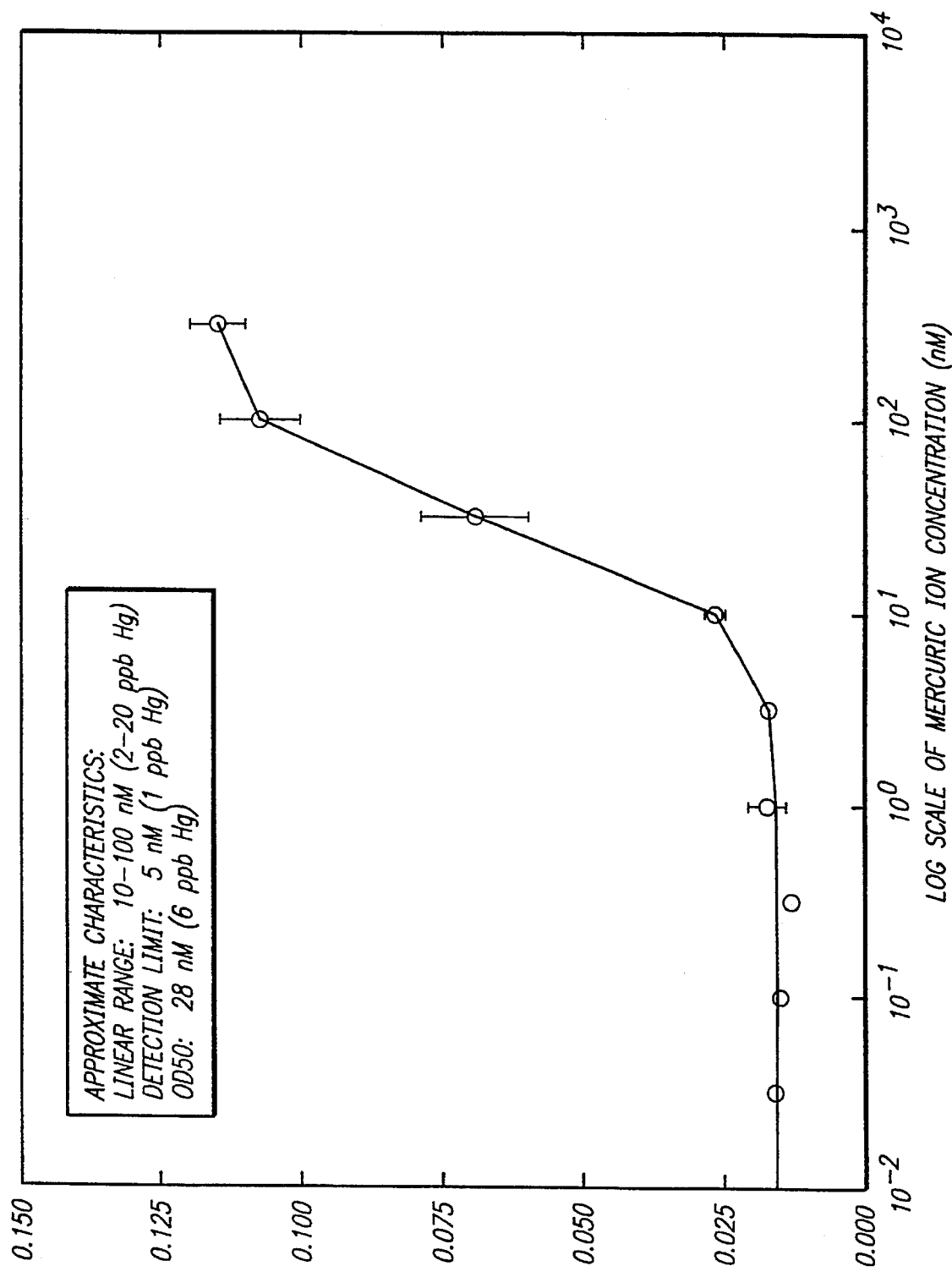
FIG. 3 shows a standard curve of the assay system based on the format shown in FIG. 4, infra. Vertical error bars represent standard deviation of quadruplicate samples.

This method of the present invention can be carried out using either a sequential incubation format or a simultaneous incubation format. Generally, in the sequential incubation format, the sample suspected of containing the metal ions is contacted with (i.e., combined with, added to, mixed with, passed over, flowed over, etc.) the first sandwich chelator (i.e., the chelating protein conjugate) immobilized on a solid support, e.g., microtiter plates. After an incubation period, the solid support is washed to remove all unbound molecules and materials. The second sandwich chelator linked to an enzyme (e.g., alkaline phosphatase, horseradish peroxidase, etc.) is then added. After an incubation period, the solid support is again washed to remove all unbound molecules and materials. Finally, the substrate required by the enzyme to produce a detectable color is added. The enzyme-catalyzed conversion of the substrate into a chromogenic product is allowed to proceed for a short color development period. Finally, the optical absorbance of the liquid in each well is read at the appropriate wavelength with an electronic plate reader (for example, ELISA-plate readers, i.e., by UV-VIS spectroscopy). A dose response curve such as the one set forth in FIG. 3 can then be generated from the data and used to determine the metal ion concentration present in the sample.

Alternatively, in the simultaneous incubation format, the solid support having the first sandwich chelator immobilized thereon is incubated simultaneously with both the sample suspected of containing the metal ion and the second solid support linked to the reporter group (e.g., an enzyme). After a sufficient incubation period, the solid support is washed to remove all unbound materials. Finally, as with the sequential incubation format, the substrate required by the enzyme to produce a detectable color is added, and the optical density is read using, for example, ELISA-plate readers (i.e., by UV-VIS spectroscopy). Again, a dose response curve can be generated from the data obtained and used to determine the metal ion concentration present in the sample.

The optical density pattern or dose response curve of the two-site assay, i.e., the sandwich assay, exhibits the "hook effect," i.e., a bell shaped standard curve (OD versus lg[concentration]). (See, Nomura, M., et al., *J. Immunol. Methods*, 56: 13–17 (1983, the disclosure of which is incorporated by reference.) The theoretical grounds for this "hook effect" are as follows: the higher the concentration of the analyte in the sample (i.e., metal ion), the more likely it is that a sandwich chelate complex will be formed between two "second (i.e., mobile) sandwich chelators" and the analyte or metal ion being detected. Since this complex is mobile (i.e., not bound to a solid support), it will be subsequently washed off, resulting in a decreasing optical density at increasing ion concentrations. The descending part of the curve is usually seen only at very high analyte concentrations. Thus, in most analyses, the assay's increasing, low-concentration, linear range is utilized. Consequently, the unknown samples must be tested at dilutions at least two orders of magnitude apart or, other preventive measures must be taken to ensure that the optical density actually falls within this interval (see, Cole, T., et al., *Clin. Chem.*, 39: 695–696 (1993), the disclosure of which is incorporated herein by reference).

Figure 4:
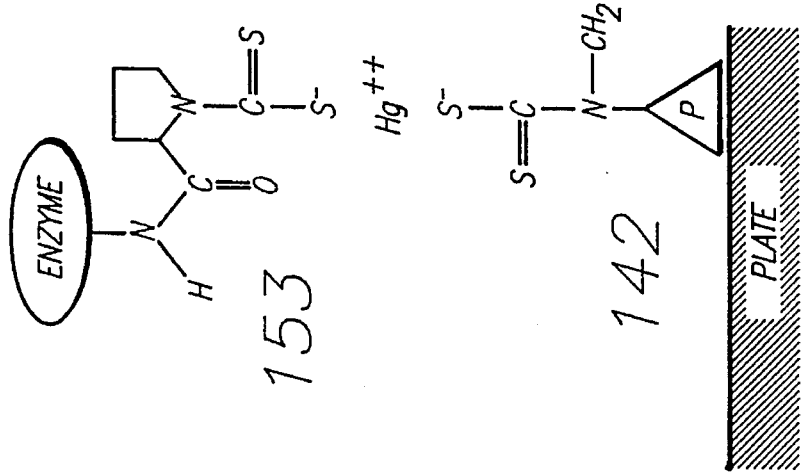
FIG. 4 sets forth the structural presentation of the assay system combining coating chelator #142 with enzyme linked chelator 153#. P (protein) represents ovalbumin. Enzyme stands for alkaline phosphatase (AP).

It has been discovered that mercury(II) ions can be conveniently and readily detected at low ppb concentrations using this method of the present invention. For instance, the standard curve (FIG. 3) of one of our sequential incubation assay systems (FIG. 4) has an $OD_{50}$ value (i.e., the metal ion concentration at which 50% of the maximum optical density is achieved) of about 6 ppb mercury(II)-ion concentration, detection limit of 1 ppb, and a linear range of 2 ppb to approximately 20 ppb. In this latter range, the optical density is proportional to the logarithm of the metal ion concentration. The metal content of an unknown solution, which has been properly diluted so that it falls within the linear range, can be accurately estimated by comparing its resultant optical density to those values represented by the standard curve. The decreasing part of the curve is not shown on FIG. 3; the optical density begins to fall at mercuric ion concentrations above about 60 ppb. The sensitivity of this assay is more than adequate for most common analytical problems. However, some environmental applications require ultra-trace level detection of mercury. In such cases, preconcentration of the samples by, for example, chelate extraction, ion-exchange chromatography, etc., can be used to further increase and enhance the sensitivity of the present assay.

In another aspect, the present invention provides a competitive method for assaying for the presence of a metal ion in a sample suspected of containing the metal ion, the method comprises: (a) contacting the sample with a solid support, the solid support having a chelator immobilized thereon in a manner such that the chelator is capable of binding with the metal ion to form a chelate complex; (b) adding to the sample an organometallic compound that is capable of binding with the chelator to form a chelate complex, the organometallic compound having immobilized thereon a reporter group; and (c) detecting the presence of the metal ion through the presence or absence of the reporter group.

As with the previously described method, this method of the present invention can be used to selectively detect and, where desired, quantitate metal ions present in a sample. More particularly, the present invention can be used to selectively detect ions of light, transition, heavy, lanthanide and actinide metals with various oxidation states. Such metal ions include, but are not limited to, the following: antimony, arsenic, beryllium, cadmium, cerium, chromium, cobalt, copper (Cu(II)), gold, lead, manganese, mercury (Hg(II)), nickel, palladium, selenium, silver, thallium, uranium, zinc and zirconium. As with the previously described method, the term "sample" refers to any sample derived from a biological (e.g., serum, urine), environmental (e.g., ground water, ponds, lakes, oceans), industrial (e.g., chemical manufacturing operations) or commercial (e.g., food products) source that is suspected of containing the metal ions of interest. Moreover, the term "contacting" is used herein interchangeably with the following: combined with, added to, mixed with, passed over, flowed over, etc.

As used herein, the term "chelator" refers to a compound that is capable of forming a complex or (interchangeably) a coordination compound with the analyte (i.e., metal ion) being detected. The chelator employed in this method of the present invention must be capable of selectively detecting the analyte of interest, and it must be capable of forming a thermodynamically stable chelate complex (i.e., a chelator-analyte complex). Examples of suitable chelators include, but are not limited to, the following: dithiocarbamates, 2,3-dimercaptopropanesulphonic acid, 2,3-dimercaptopropanol-1, D,L-penicillamine, 2-(3-sulfobenzoyl)pyridine-2-pyridylhydrazone, selenohydryl-containing compounds, 4-(2-pyridylazo)resorcinol, diphenylthiocarbazone, 1-(2-pyridylazo)-2-naphthol, 6-amino-1-naphthol-3-sulphonic acid, histidine and acetylacetone. The particular chelators used in this method of the present invention will depend on which metal ion is being detected, and the selection in any given case will be apparent to those of skill in the art (see, infra, for a detailed discussion regarding the particular chelators which are useful for detecting the various metal ions).

Moreover, it will be readily apparent to those of skill in the art that this method of the present invention is not limited to the use of the foregoing chelators. To be useful in the method of the present invention, the chelator must be capable of selectively detecting the analyte of interest, and it must be capable of forming a chelate complex (i.e., a chelator-analyte complex). As such, any complexing agent (i.e., those presently known or those developed in the future) that is capable of selectively forming sandwich chelates of high thermodynamic stability with the target analyte under appropriate kinetics (i.e., fast rate of formation relative to analysis time) can be used to carry out the detection method of the present invention. In a presently preferred embodiment, mercuric ions are the metal ions that are quantitatively detected. As such, dithiocarbamates are employed as the chelator in this particular method as these compounds have very high affinities for mercury(II) ions.

It will be further understood by those of skill in the art that the pH of the buffer, the ionic strength of the buffer, the presence of a masking agent (i.e., extra chelating reagent added to the system to decrease interferences with foreign ions), etc., can influence the selectivity of the assay. By running routine titration experiments, such as those set forth herein below, one of skill in the art can optimize the reaction conditions for the particular chelator being used and the particular metal ion being detected.

In this method of the present invention, the chelator is immobilized on or bound to a solid support or solid phase (i.e., an insoluble polymeric material, inorganic or organic matrix, gel, aggregate, precipitate or resin) in a manner such that it is capable of binding with the metal complex to form a chelate complex, i.e., chelate-metal ion complex. Preferred solid supports in accordance with the present invention include, but are not limited to, the following: cellulose, agarose, dextran, polyacrylate, polyacrylamide, polystyrene, polyvinyl chloride, or their derivatives, chitin, sepharose, oxirane substituted acrylic beads, starch, oxidized starch (i.e., polymeric dialdehyde), collagen, keratin, elastin, bovine hide powder, bacterial cell wall peptidoglycan or fragments thereof, diazotized paper, nylon, polyethylene terephthalates, polycarbonates, metallic particles and controlled pore glass. Of these, certain solid supports are presently preferred, namely, cellulose and cellulose derivatives (e.g., nitrocellulose), agarose, dextran, polyacrylate, polyacrylamide, polystyrene, polyvinyl chloride and glass. Even more preferred for use as a solid support are nitrocellulose, polystyrene and polyvinyl chloride. Polystyrene and polyvinyl chloride are normally used as microtiter plates, while nitrocellulose is normally used in sheets.

Immobilization of the chelator onto the solid support is carried out using conventional methods and procedures known to and understood by those skilled in the art. As previously mentioned, the chelator can be immobilized on the solid support through the use of a cross-linking reagent and, if necessary, a linker molecule or (interchangeably) a spacer molecule. As such, the previous discussion pertaining to the use of cross-linking agents to link the first sandwich chelator to the solid support is fully applicable here. Using the cross-linking reagents set forth above, one of ordinary skill in the art can readily link the chelator to the solid support using conventional coupling reactions known in the art.

In a presently preferred embodiment, proteins are the linker molecules used to attach the chelator to the solid support. Such proteins include, but are not limited to, the following: bovine serum albumin, conalbumin, keyhole limpet hemocyanin and ovalbumin. Moreover, in a further preferred embodiment of the present invention, the chelator linked to a protein (e.g., BSA, CONA, KLA, OVA, etc.) is doped on the surface of a polystyrene or polyvinyl chloride microtiter plate (i.e., an ELISA plate) using the methodology applied in the immunoassay field for coating microtiter plates. It will be readily apparent to those of skill in the art, however, that other methods can be used to attach the chelator to the solid phase or support. As such, the mode of attaching the chelator to the linker molecule and, in turn, the solid support is not a critical feature of the present invention.

In this method of the present invention, an organometallic compound is used as the compound which competes with the metal ions present in the sample for the chelator. The organometallic compound has a reporter group or (interchangeably) a reporter system immobilized thereon or linked thereto. As used herein, the term "organometallic compound" refers to a compound that contains carbon-metal bonds. The nature of the carbon-metal bonds varies widely, ranging from bonds that are essentially ionic to those that are primarily covalent. For purposes of the present invention, the structure of the organic portion of the organometallic compound is not critical; all that is required is that the metal portion of the organometallic compound be accessible so that it can form a complex with the chelator. Moreover, it is not essential that the metal present in the organometallic compound be the same as the metal ion being detected or quantitated in the sample. All that is required is that the metal portion of the compound has an affinity for the chelator, and that it be accessible so that it can form a complex with the chelator. As such, a wide variety of organometallic compounds can be used as the competing compound in this method of the present invention.

Organometallic compounds suitable for use in the present invention are frequently prepared from olefins, organic halides, aromatic compounds, diazonium salts, etc., using standard techniques and protocols known to those skilled in the art. (See, e.g., Carey, F. A. & Sundberg, R. J., *Advanced Organic Chemistry. Part B: Reactions and Synthesis* (Plenum Press, New York, 1980); and Wilkinson, G., et al., *Comprehensive Organometallic Chemistry. The Synthesis, Reactions and Structures of Organometallic Compounds.* Vols 1–9 (Pergamon Press, Oxford, N.Y., 1982) the disclosure of which are incorporated herein by reference.) It will be readily apparent to those of skill, however, that other methods can be used to prepare organometallic compounds suitable for use in the present invention. As such, the method used to prepare such compounds is not a critical feature of this invention.

Moreover, as used herein, the term "reporter group" refers to any moiety, molecule, atom or species that results in a detectable signal or change when the analyte of interest (e.g., metal ion) is present in the sample. As previously mentioned, the reporter group can, itself, be a detectable signal (i.e., a detectable label, e.g., $^{125}$I) or, alternatively, the reporter group can be capable of undergoing a detectable change or of bringing about a detectable change. Suitable reporter groups in accordance with the present invention, include, but are not limited to, the following: enzymes, chromogens, fluorophores, radioisotopes and biotin, or to these groups attached to an antibody that recognizes the chelate complex. It should be understood that the prior discussion pertaining to the use of the various reporter groups and reporter systems is fully applicable to this method of the present invention. Moreover, it should be understood that the organometallic compound can be linked to the reporter group or reporter system using coupling reactions similar to those used for linking the chelator to the solid support. As such, the prior discussion pertaining to the use of cross-linking reagents is fully applicable here.

As with the previously described method, the competitive assay method of the present invention can be carded out using either a sequential incubation format or a simultaneous incubation format. In the sequential incubation format, either the test sample or the organometallic compound attached or bound to the reporter group is contacted first with the chelator immobilized on the solid support. Depending upon which component is contacted with the immobilized chelator in the first step, the remaining component is added in the second step. In contrast, in the case of the simultaneous incubation format, the sample and the organometallic compound (either pre-mixed or added simultaneously) are contacted with the immobilized chelator in a single step.

Figure 5:
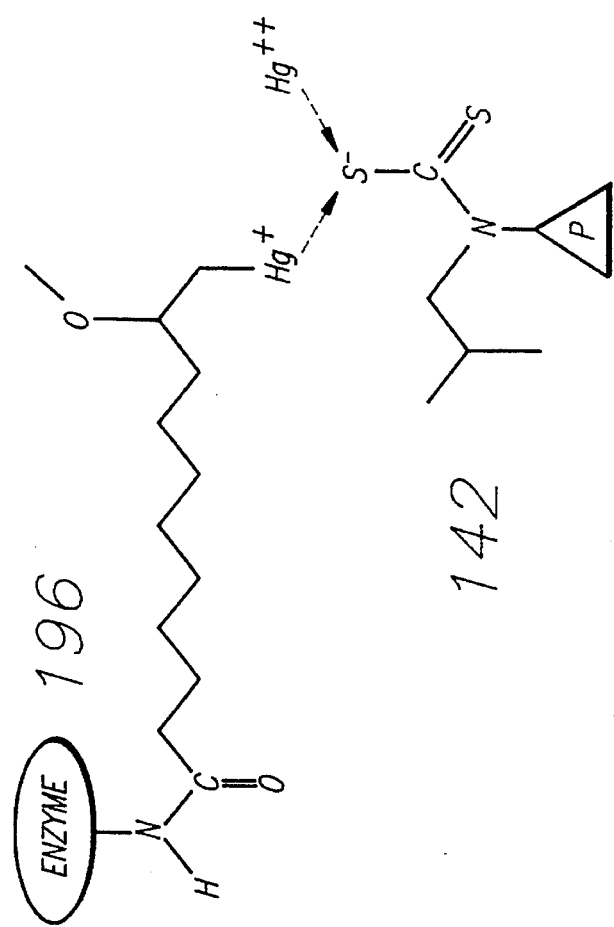
FIG. 5 shows the competitive format of the enzyme amplified metal complex assay exemplified by the system #142-CONA/#196-AP. Structures of the dithiocarbamate chelator linked to the plate coating conjugate (#142-CONA) and of the mercury containing group linked to an enzyme (#196-AP).

An example of this competitive assay format is set forth in FIG. 5. In this assay, an organomercuric compound is attached to the reporter system, i.e., an enzyme, while the sulfur containing chelator is attached or bound to the solid support (see, FIG. 5, system #196AP/#142-CONA). Using this competitive assay format, one can detect metal ions at ppb/ppt concentrations. Moreover, using this competitive assay format, the quantity, i.e., concentration, of the metal ion present in the sample can be quantitated by the amount of the organometallic compound that is bound to the chelator and, in turn, the solid support. Since the amount of organometallic compound that is bound to the chelator will be inversely proportional to the quantity of metal ion present in the sample, the optical density response will also be inversely proportional to the quantity of metal ion present. A standard curve such as the one in FIG. 10 can be generated. Samples containing unknown concentrations of metal can be evaluated and the concentration of metal ion determined by diluting them so that their corresponding optical density responses fall within the standard curve's linear range It will be understood by those of skill in the art that the opposite arrangement is also possible, i.e., the organometallic compound is immobilized on the solid support (e.g., the surface of the microtiter plate), while the chelator is bound to the reporter enzyme or other reporter system. As such, this competitive method for assaying for the presence of a metal ion comprises: (a) contacting the sample with a chelator that is capable of binding with the metal ion to form a chelate complex, the chelator having immobilized thereon a reporter group; (b) contacting the sample with a solid support, the solid support having an organometallic compound immobilized thereon in a manner such that the organometallic compound is capable of binding with the chelator to form a chelate complex; and (c) detecting the presence of the chelate complex and, in turn, the metal ion through the presence or absence of the reporter group. As with the previously described competitive assay method, this arrangement of the competitive assay format can be carded out using either a sequential incubation format or a simultaneous incubation format.

In a further aspect, the present invention provides a kit for assaying for the presence of a metal ion in a sample suspected of containing the metal ion, the kit comprising: a solid support having a first sandwich chelator immobilized thereon in a manner such that the first sandwich chelator is capable of binding with the metal ion to form a chelate complex; and a second sandwich chelator, the second sandwich chelator having a reporter group immobilized thereon in a manner such that the second sandwich chelator is capable of binding with the chelate complex to form a sandwich chelate complex. The kit may also comprise the detection, visualization or tagging material required by the reporter group for determination of the presence of the sandwich chelator complex, i.e., the chelator-analyte-chelator complex, and, in turn, the metal ion.

In yet another aspect, the present invention provides a kit for competitively assaying for the presence (and quantity) of a metal ion in a sample suspected of containing the metal ion, the kit comprising: a solid support having a chelator immobilized thereon in a manner such that the chelator is capable of binding with the metal ion to form a chelate complex; and an organometallic compound that is capable of binding with the chelator to form a chelate complex, the organometallic compound having immobilized thereon a reporter group. As with the previously described kit, this kit may also comprise the detection, visualization or tagging material required by the reporter group for determination of the presence or absence of the metal ion.

It will be readily apparent to those of skill in the art that the methods and kits of the present invention can be used for detecting targets other than metal ions. For example, the method of the present invention is fully applicable for the detection of cations other than metal ions, anions, zwitterions, radicals, and organic compounds with neither charge nor unpaired electrons. There are a wide range of binding forces that can be utilized in the method of the present invention. Such binding forces include, but are not limited to, the following: hydrogen bonds, hydrophobic forces, charge transfer stabilization, and even covalent bonds.

Moreover, the assay formats for the methods of the present invention are not restricted to the ELISA-type methodology. Other suitable formats include, but are not limited to, assay with radiolabels, flow-through columns, dipstick formats, and sensors. Numerous types of sensors have been reported in the literature; the most important of which are based on electrochemical and optical transduction, both possibly involving enzymatic amplification (see, e.g., Hilditch, P., et al., *Analyst*, 116: 1217–1220 (1991); Ivnitskii, D., et al., *Anal. Chim. Acta.*, 261: 45–52 (1992); Anis, N., et al., *J. Agric. Food Chem.*, 41: 843–848 (1993); Griffits, D., et al., *Trends Biotechnol.*, 11: 122–130 (1993); and Wang, J., *J. Anal. Chem.*, 65: 450R–453R (1993), the disclosure of which are incorporated herein by reference). Depending on the analyzer concept, such devices operate off line (e.g., disposable sensor for the analysis of discrete samples), on line (e.g., flow injection systems), and in line (e.g., implantable sensor, in situ application for continuous environmental monitoring). The basic principle of the sandwich complex assay, i.e., the use of the sandwich chelate complex as the chemical recognition system, can be adapted for most of the known sensor forms. Moreover, the assay can be formatted for many purposes ranging from highly precise laboratory analysis, to integrated process controllers, to field portable assays for on-site monitoring.

All references and publications mentioned hereinabove are hereby incorporated in their entirety by reference.

The invention will now be described in greater detail by way of specific examples. The following examples are offered for illustrative purposes, and are intended neither to limit the invention in any manner. Variations within the concepts of the invention will be apparent to those skilled in the art.

EXAMPLES

The following protocols and experimental details are referenced in the examples that follow. All references mentioned hereinbelow are hereby incorporated in their entirety by reference.

A. Abbreviations Used and General Procedures

AP, alkaline phosphatase; BSA, bovine serum albumin; CONA, conalbumin; DMF, dimethylformamide; EDC, 1-(3-dimethylaminopropyl)-3-ethylcarbodiimide hydrochloride; ELISA, enzyme-linked immunosorbent assay; HRP, horseradish peroxidase; KLH, keyhole limpet hemocyanin; N-hydroxysulfosuccinimide, (±)-1-hydroxy-2,5-dioxo-3-pyrrolidinesulfonic acid; OD, optical density; $OD_{50}$: analyte concentration results in 50% of maximum optical density; OVA, ovalbumin; PBS, 0.2M phosphate-buffer plus 0.8% NaCl (pH 7.5); THF, tetrahydrofuran; TMB, 3,3',5,5'-tetramethylbenzidine.

The system of codes used for the identification of the products of the coupling reactions is shown by the following examples:

the first 3 digits (e.g., 149) refer to the chemical structure of the hapten;

the first letter shows which experiment the conjugate was produced in (e.g., A in 149A); and the second letter shows which protein or enzyme was conjugated as follows: 149AB: BSA; 149AC: CONA; 149AK: KLH; 149AO: OVA; 149AA: AP; 149AR: HRP.

A Sybron/Barnstead Nanopure II water purification system provided water (16.7 megohm/era) nanopure water for the preparation of aqueous solutions. The obtained conjugates were purified by exhaustive dialysis at 4° C. in 4–5 L volumes with stirring. At least 6 hours passed between consecutive changes of the dialysis buffer. (The number of changes of the dialysis buffer is given in parentheses after each experiment, e.g., 6×.) High enzymatic activity was demonstrated after all chemical procedures with enzymes and enzyme conjugates. Protein conjugates were stored at −20° C. Enzyme derivatives were kept at 4° C. for short periods. Long term storage of enzyme conjugates, after being mixed with equal volume of ethylene glycol, was performed at −20° C. with no significant loss of enzymatic activity in several months. Nunc-Immuno Plate Brand 96-well polystyrene microtiter plates (Nunc InterMed, Denmark) were used in the assays. A $V_{max}$ electronic microplate reader (Molecular Devices, Menlo Park, Calif.) was employed to measure the optical absorbance of the chromogenic products at the appropriate wavelength. The buffers (e.g., 50 mM carbonate buffer at pH 9.6 for coating, 100 mM sodium acetate buffer at pH 5.5) used in the assays were purified by passing them through columns of Chelex 100 Brand ion exchange resin (Bio-Rad Laboratories, Richmond, Calif.) to remove the traces of mercury and other potentially interfering metal ions (Holmquist, B., *Methods Enzymol.*, 158: 6–12 (1988)). Most of the immunochemicals, e.g., proteins (BSA, CONA, OVA, KLH), AP (7.2 or 17 mg protein/mL dissolved in 3.0M NaCl solution containing 1 mM of $MgCl_2$, 0.1 mM of $ZnCl_2$, and 30 mM of triethanolamine, pH 7.6, activity: 2600 units/mg protein [pH 9.8 at 37° C.], product number: P-0405), disodium p-nitrophenyl phosphate, and TMB were purchased from Sigma Chemicals Co. (St. Louis, Mo.). HRP was obtained from Boehringer (Mannheim, Germany). Common solvents and chemicals, e.g., N-hydroxysulfosuccinimide monosodium salt (97%), EDC, were obtained from Aldrich Chemical Co. (Milwaukee, Wis.) if not otherwise stated.

B. General Procedures For the Syntheses of the First and Second Sandwich Chelators In several of the examples set forth below, secondary amino groups were formed by reductive amination of primary amino groups (e.g., ε-amino groups of the lysine derivatives) on the surface of proteins and enzymes by carbonyl compounds (e.g., aldehydes or ketones) and sodium tetrahydroborate (i.e., experiments #141 and #158). In such a reaction, the use of reducing agents other than sodium tetrahydroborate (Means and Feeney, *Biochemistry*, 7: 2192–2201(1968)) such as, for example, sodium cyanohydridoborate (Borch, et al., *J. Amer. Chem. Soc.*, 93: 2897–2904 (1971)) and amine boranes (Cabacungan, J., et al., *Anal. Biochem.*, 124: 272–278 (1982); Wong, W., et al., *Anal. Biochem.*, 139: 58–67 (1989); Stults, N., et al., *Anal. Biochem.*, 180: 114–119 (1989); Tainturier, G., et al., *J. Agric. Food Chem.*, 40: 760–763 (1992) can also be used. Additionally, electrochemical reduction to produce the secondary amino group is also a possibility (see, Tainturier, et al., ibid., 40: 760–763 1992).

Alternatively, a N-protected secondary amine bearing another group for the conjugation to the biopolymers can also be employed in the synthesis of the chelators. This approach was used to prepare the L-prolyl derivatives (experiments #149 and #152).

N-Trifluoroacetyl-L-proline was conjugated by a novel method using a combination of water soluble carbodiimides and N-hydroxysulfosuccinimide, which enhances the carbodiimide-mediated coupling reactions of haptenic carboxylic acids to proteins (Staros, J., et al., *Anal. Biochem.*, 156: 220–222 (1986); Anjaneyulu, P., et al., *Int. J. Pept. Protein Res.*, 30: 117–124 (1987); Bekheit, H., et al., *J. Agric. Food Chem.*, 41 (1993). The transformation of a hapten, insoluble in water, to a reactive intermediate, the corresponding N-hydroxysulfosuccinimide ester, with higher water solubility usually results in improved coupling efficiency to proteins in aqueous solution. This technique also minimizes the amount of the organic cosolvent used in the conjugation procedure, which is of a definite advantage in the synthesis of enzyme tracers in terms of preserving high enzymatic activity.

This synthetic pathway requires the cleavage of the N-blocking group. In contrast, the present method for the removal of the N-trifluoroacetyl (TFA) group is based on the report by Weygand, F., et al., *Chem. Ber.*, 103: 2437–2449 (1970) on the special case of the reductive cleavage of the N-terminal protecting group in N-TFA-prolyl peptides. The attachment of the blocked proline and the splitting of the TFA group by sodium tetrahydroborate was confirmed by F-NMR-spectroscopy in the case of the BSA conjugate.

There are further possible synthetic strategies to generate secondary amino groups on proteins. For instance, a biomacromolecule, derivatized first by a bifunctional hapten with a carbonyl and a reactive group for coupling, can be converted to the target structure by reductive amination of the carbonyl moiety.

C. General Procedures for the Syntheses of the Metal Containing Reagents

An organomercury compound, $^+Hg$—$CH_2$—$CHX$—$(CH_2)_8$—$CO_2H$ (X: $OCH_3$) was obtained by methoxymercuration of 10-undecenoic acid ($CH_2$=$CH$—$(CH_2)_8$—$CO_2H$). (It will be understood by those of skill in the art that homologues and similar compounds having different X-substitutents can be similarly prepared.) The mercury containing acid was then linked to proteins and enzymes by means of water soluble carbodiimide and N-hydroxysulfosuccinimide. (See, FIG. 5 for the structure of the HRP-conjugate.) Various other organomercury compounds having the mercury atom attached through a carbon or heteroatom can be used in this assay. Moreover, other classes of organometallic compounds may be used in this type of assay.

D. Preparation Of the First and Second Sandwich Chelators

Figure 6B:
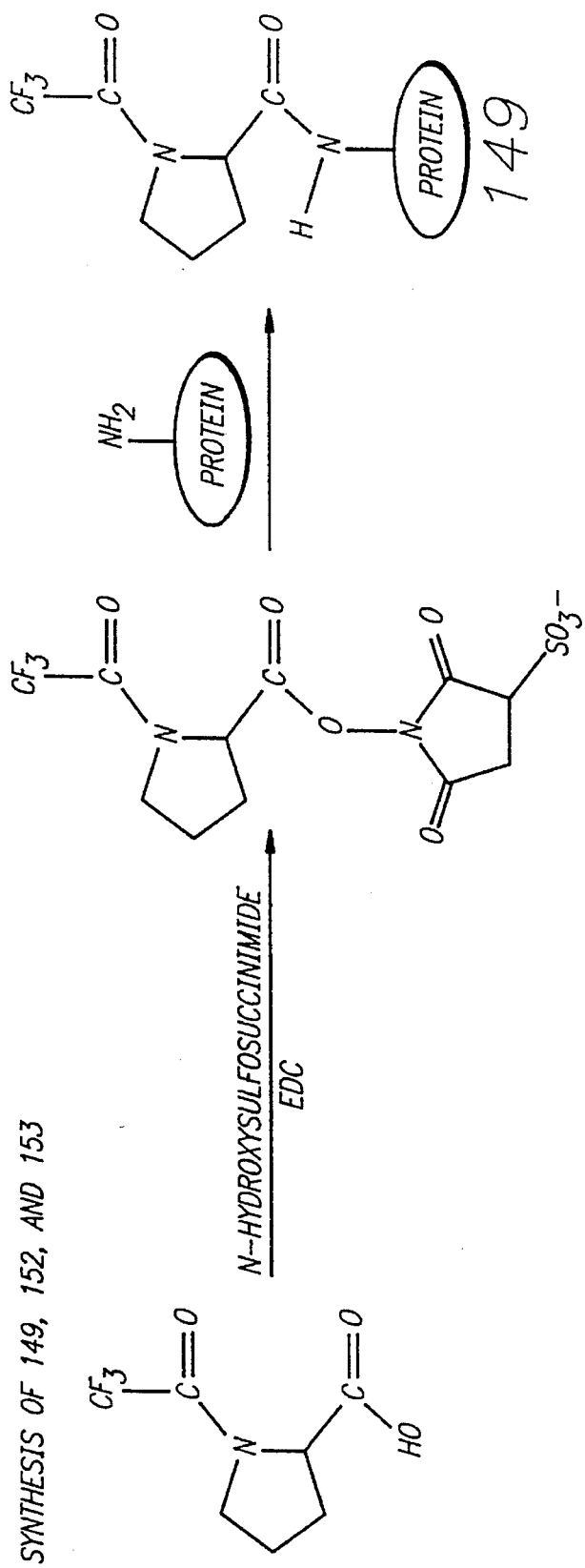
Figure 6B:
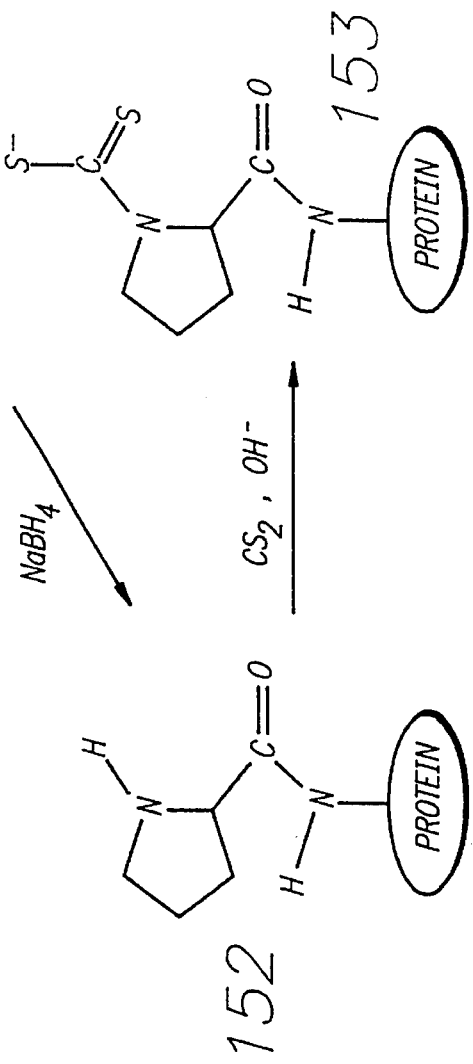
Figure 7B:
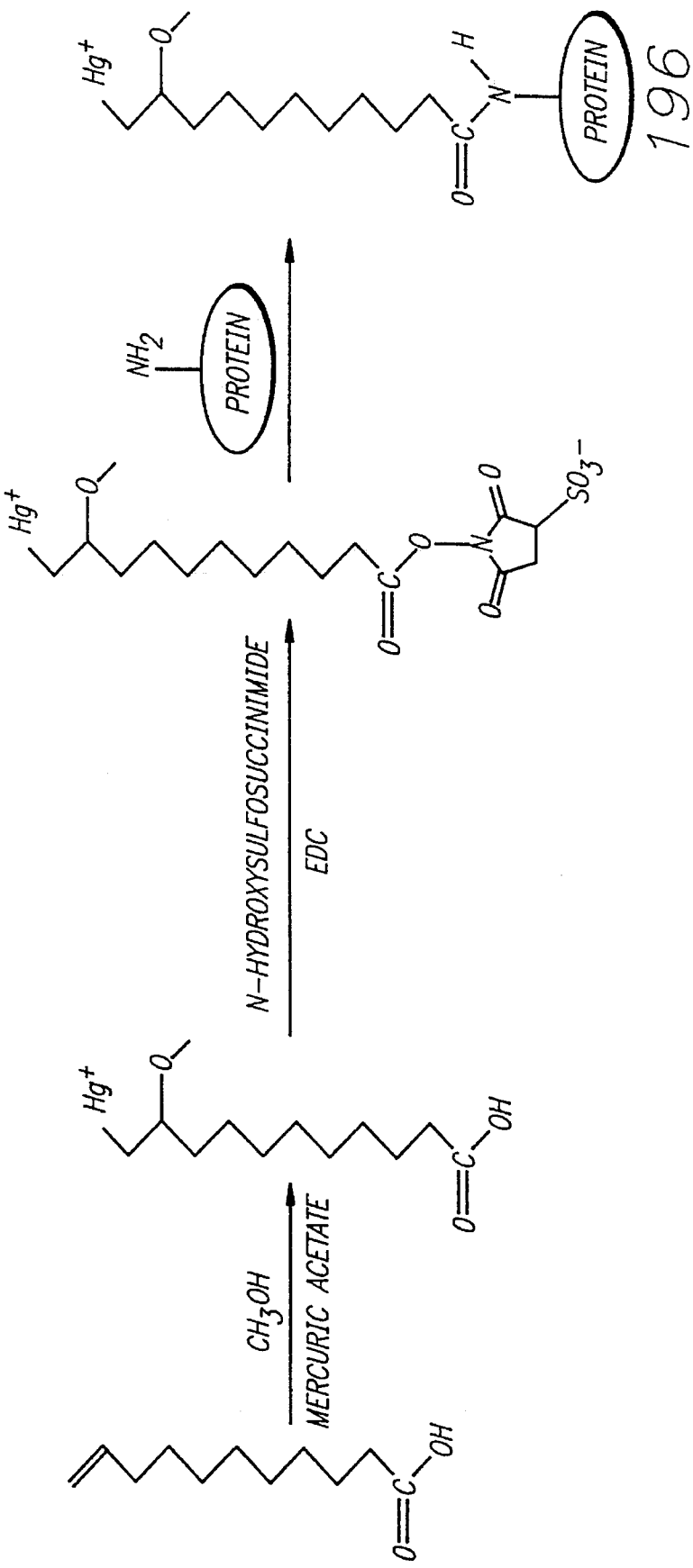

FIGS. 6 and 7 set forth the reaction schemes used to prepare the dithiocarbamate chelators and organometallic compounds used in the methods of the present invention. For details of the protocols used, please refer to the experiments set forth hereinbelow.

1. Experiments #141 a. Experiment #141A

The reactions were carried out in teflon-capped glass vials with vigorous magnetic stirring. Proteins (BSA, CONA, KLH, OVA: 10 mg of each) dissolved in a 1:1 mixture of water and PBS (12 mL for each protein) were ice-cooled. Isobutyraldehyde (0.3 mL, 3.3 mmol, d: 0.794) in mL of THF (3 mL) was added dropwise to each aqueous protein solution at 4° C. over several minutes. The reaction mixtures were stirred at 4° C. for 15 minutes, at 10° C. for one hour, and ice-cooled again. Sodium tetrahydroborate (100 mg, 2.64 mmol for each) was then added portionwise to the mixtures at 4° C. over several minutes. The reaction mixtures were stirred at the same temperature for 30 mins and at room temperature overnight. The protein conjugates (141AB, 141AC, 141AK, and 141AO) were purified by dialysis in PBS (5×).

The conjugation reaction of AP was performed at 4° C. AP solution (0.06 mL, 0.43 mg of enzyme) was admixed with cold 0.15M borate buffer (pH: 9, 7.5 mL) and water (3 mL). Isobutyraldehyde (5 µl) in THF (0.1 mL) was added with stirring, and the reaction mixture was stirred for 2 hours. Sodium tetrahydroborate (7.5 mg) was then added portionwise. The mixture was stirred for one hour. The conjugate (141AA) was purified by dialysis in PBS (5×).

b. Experiment #141B

The reactions were carded out in a round bottom flask with vigorous magnetic stirring at 4°–6° C. Proteins (BSA, CONA, OVA: 100 mg of each) dissolved in a 1:1 mixture of water and PBS (15 mL for each) were ice-cooled. Isobutyraldehyde (0.5 mL, 5.5 mmol) in THF (3 mL) was added dropwise to each protein solution over several minutes, then the reaction mixtures were stirred for one hour. Sodium tetrahydroborate (100 mg, 2.64 mmol for each) and water (2 mL for each) were then added portionwise to the reaction mixtures in several minutes. The mixtures were stirred for 3 hours. The protein conjugates were purified by dialysis in PBS (6×). Some denaturation occurred during the procedure, especially in the case of 141BO, thus the solid precipitate was removed by centrifugation. The protein content of the conjugate solutions was determined (141BB: 3.8 mg/mL, 141BC: 2.2 mg/mL, and 141BO: 0.7 mg/mL).

2. Experiments #142 a. Experiment #142A

The reactions were carried out in teflon-capped glass vials with vigorous magnetic stirring at 4° C. Protein conjugates 141AB, 141AC, 141AK, and 141AO (3.5 mL each) obtained in experiment #141A were diluted with water (1.5 mL each). The pH value of the solutions were adjusted to about 10 by 1M NaOH solution. 0.5 mL of 0.1M carbon disulfide solution in THF was added dropwise, then the reaction mixtures were stirred for 3 hours. The conjugates (142AB, 142AC, 142AK, and 142AO) were purified by dialysis in water (4×).

Enzyme conjugate solution 141AA (10.5 mL) was diluted with cold 0.13M bicarbonate/carbonate buffer (pH: 9.6, 8 mL). 0.1M Carbon disulfide solution in THF (0.2 mL) was added dropwise in several minutes, then the reaction mixtures were stirred for 4½ hours. The conjugate (142AA) was purified by dialysis in PBS (7×).

b. Experiment #142B

The reaction was carded out in a teflon-capped glass vial with magnetic stirring at 4° C. Protein conjugate 141AB (7 mL) obtained in experiment #141A were diluted with water (3.5 mL) and PBS (7 mL), then the mixture was cooled in ice. The pH value of the solution was adjusted to about 10 by 0.1M NaOH solution. 0.5 mL of 0.1M carbon disulfide solution in THF was added dropwise, then the reaction mixture was stirred at 4° C. for 4 hours while pH value of 9–10 was maintained by occasional addition of 0.1M NaOH solution. The conjugate (142BB) was purified by dialysis in PBS (5×).

c. Experiment #142C

The reaction was carried out in a teflon-capped glass vial with magnetic stirring at 4° C. throughout. Protein conjugates (141BB: 2.63 mL, 141BC: 3.68 mL, 141BO: 10 mL) obtained in experiment #141B were diluted with cold 0.13M bicarbonate/carbonate buffer (pH: 9.7, 13.5 mL for each). 0.1M Carbon disulfide solution in THF (0.3 mL for each) was added dropwise in several minutes, then the reaction mixtures were stirred for 7 hours. The conjugates (142CB, 142CC, and 142CO) were purified by dialysis in PBS (6×).

3. Experiment #149A

The reactions were carried out in a teflon-capped glass vials with magnetic stirring. N-Trifluoroacetyl-L-proline (Steglich, W., et al., *Synthesis*, 399–401 (1976) (22.9 mg, 108.5 μmol), N-hydroxysulfosuccinimide monosodium salt (38.7 mg, 173 μmol), and then EDC (24.9 mg, 130 μmol) were added to dry DMF (7 mL). The reaction mixture was stirred vigorously under nitrogen at room temperature for one day. The formed solution was divided into 6 aliquots.

Proteins (BSA, CONA, OVA: 30 mg of each, KLH: 15 mg) dissolved in PBS (7 mL each), were ice-cooled. 20% volume of the DMF solution (see above) was added dropwise to each ice-cooled protein solution with vigorous stirring in several minutes. The reaction mixtures were stirred at 4° C. for one hour, and then at room temperature overnight. The formed conjugates (149AB, 149AC, 149AK, 149AO) were purified together with 149AA (see below) by dialysis in PBS (5×).

AP solution (0.3 mL, 2.2 mg of enzyme) was admixed with ice cold PBS (16 mL). 10% volume of the DMF solution was added dropwise to the vigorously stirred enzyme solution at 4° C. within several minutes. The reaction mixture was stirred at the same temperature overnight. The formed conjugate (149AA) was purified together with the protein derivatives (e.g., 149AB, see above) by dialysis in PBS (6×).

HRP (2.0 mg) was conjugated by a procedure identical with that of 149AA (see above) except that 0.13M NaHCO$_3$ solution was used instead of PBS. The formed conjugate (149AR) was purified by dialysis in 0.13M NaHCO$_3$ (6×).

4. Experiment #152A

The reactions were carried out in teflon-capped glass vials with magnetic stirring at 4° C. throughout. Solutions of protein and enzyme conjugates (149AB: 4.7 mL, 149AC: 4.2 mL, 149AK: 5.3 mL, 149AO: 5.7 mL, and 149AR: 2.8 mL) obtained in the previous experiment were given to cold 0.13M bicarbonate/carbonate buffer (pH: 9.6, 10 mL for each protein, 17 mL for 149AR), then sodium tetrahydroborate (25 mg for each protein, 1.5 mg for 149AR) was added portionwise to the reaction mixtures in several minutes. The mixtures were stirred for 22 hours, and then subjected to purification by dialysis in PBS (7×) for the protein conjugates (152AB, 152AC, 152AK, and 152AO), in 0.13M NaHCO$_3$ (7×) for 152AR.

Sodium tetrahydroborate (3.7 mg) was added to cold PBS (pH: 9.5, 17 mL), then the reaction was initiated by addition of the enzyme conjugate 149AA (2 mL) to the mixture. After 8 hours, another portion of sodium tetrahydroborate (1.2 mg) was added to the reaction mixture, then it was stirred for 14 hours. The conjugate (152AA) was purified by dialysis in PBS (6×).

5. Experiments #153 a. Experiment #153A

The reactions were carried out in teflon-capped glass vials with magnetic stirring at 4° C. throughout. Protein conjugates obtained in the previous experiment (152AB: 3 mL, 152AC: 2 mL, 152AK: 2 mL, and 152AO: 2 mL) were diluted with 0.13M bicarbonate/carbonate buffer (pH: 9.6, 4.5 mL for 152AB, 4 mL for each of 152AC, 152AK, and 152AO). 0.1M Carbon disulfide solution in THF (0.1 mL for each) was added dropwise in several minutes, then the reaction mixtures were stirred for 5 hours. The conjugates (153AB, 153AC, 153AK and 153AO) were purified by dialysis in PBS (8×).

The pH value of the cold, stirred enzyme conjugate solutions obtained in the previous experiment (152AA: 10 mL, 152AR: 7 mL) was adjusted to 9.6–9.7 by dropwise addition of diluted NaOH solution. 0.1M Carbon disulfide solution in THF (0.2 mL for each) was added dropwise in several minutes, then the reaction mixtures were stirred for 6 hours. The conjugates were purified by dialysis in PBS (6×) for 153AA and in 0.13M NaHCO$_3$ (6×) for 153AR.

b. Experiment #153B

The reaction was carried out in teflon-capped glass vials with magnetic stirring at 4° C. The pH value of the cold, stirred conjugate solution obtained in experiment #152A (152AA: 9.5 mL) was adjusted to 9.7 by dropwise addition of 0.1M NaOH solution. 0.1M Carbon disulfide solution in THF (0.2 mL) was added dropwise in several minutes, then the reaction mixture was stirred for 5½ hours while a pH value of 8–10 was maintained by occasional addition of 0.1M NaOH solution. The reaction mixture was subjected to purification by dialysis in PBS (5×) to furnish conjugate 153BA.

6. Experiment #158A

The reactions were carried out in teflon-capped glass vials with vigorous magnetic stirring. Proteins (BSA, CONA, OVA: 20 mg of each, KLH: 10 mg) were added to the ice-cooled mixture of acetone (0.5 mL for each) and 0.15M borate buffer (pH: 9, 5 mL for each). The reaction mixtures were stirred at 4° C. for one hour, diluted with 0.15M borate buffer (pH: 9, 2.5 mL for each), then stirred at room temperature for one hour. Sodium tetrahydroborate (50 mg) was added to the reaction mixture portionwise at 4° C. over several minutes, then it was stirred at the same temperature overnight. The conjugates (158AB, 158AC 158AK, and 158AO) were purified by dialysis in PBS (7×).

Enzyme conjugate 158AA was obtained in a similar way except 4° C. was maintained throughout the operations. AP solution (0.05 mL, 0.36 mg of enzyme) was added to the ice-cooled mixture of acetone (0.25 mL) and 0.15M borate buffer (pH: 9, 2.5Ml). After one hour, the reaction mixture was diluted with 0.15M borate buffer (pH: 9, 2.5 mL), then sodium tetrahydroborate (32 mg) was added portionwise. The mixture was stirred for 2 hours, then it was subjected to purification by dialysis in PBS (8×).

7. Experiment #160A

The reactions were carried out in teflon-capped glass vials with magnetic stirring at 4° C. Protein conjugates obtained in the previous experiment (158AB: 8.5 mL, 158AC: 9.5 mL, 158AK: 9 mL, 158AO: 3.2 mL) were diluted with 0.13M bicarbonate/carbonate buffer (pH: 9.6, 7.5 mL for each). 0.1M Carbon disulfide solution in THF (0.3 mL for each) was added dropwise in several minutes, then the reaction mixtures were stirred for 15 hours. The conjugates (160AB, 160AC, 160AK and 160AO) were purified by dialysis in PBS (7×).

Enzyme conjugate 160AA was obtained in a very similar way. Conjugate 158AA (7.5 mL) was diluted with 0.13M bicarbonate/carbonate buffer (pH: 9.6, 7.5 mL). 0.1M Carbon disulfide solution in THF (0.1 mL) was added dropwise in several minutes, then the reaction mixture was stirred for 2 hours. 0.1M Carbon disulfide solution in THF (0.1 mL) was added dropwise again, and the mixture was stirred for 2 hours. The conjugate was purified together with the corresponding protein conjugates by dialysis in PBS (7×).

8. Experiment #196A

The reactions were performed in teflon-capped glass vials with magnetic stirring. Solutions of 10-undecenoic acid (98%, 37.6 mg, 0.20 mmol) in THF (2 mL) and mercuric acetate (63.7 mg, 0.20 mmol) in methanol (2 mL) were admixed and stirred overnight. N-Hydroxysulfosuccinimide monosodium salt (49.3 mg, 0.22 mmol), and then EDC (42.2 mg, 0.22 mmol) were added to the ice cooled reaction mixture. After stirring at 4° C. for 15 minutes and at room temperature for 9 hours, DMF (8 mL) was added to enhance solubility. The mixture was stirred at ambient temperature overnight, then it was divided into 5 equal aliquots.

Proteins (BSA, CONA, OVA: 30 mg of each) were dissolved in 0.13M $NaHCO_3$ (12 mL each). One aliquot of the above reaction mixture was added dropwise to each ice-cooled protein solution with vigorous stirring in several minutes. The reaction mixtures were stirred at 4° C. for one hour, then at room temperature overnight. AP (17 mg/mL solution, 60 μL, 1.0 mg of enzyme) and HRP (2.6 mg) were conjugated in the same way except 4° C. was maintained throughout the operations. The conjugates (196AB, 196AC, 196AO, 196AA, and 196AR, resp.) were purified by dialysis in 0.13M $NaHCO_3$ (5×).

E. Examples of Performing the Non-Competitive Assay

As in a direct two-site or (interchangeably) "sandwick" enzyme immunoassay, the first step in performing the enzyme amplified sandwich complex assay is the adsorption of the first sandwich chelator onto a solid support or solid phase from a liquid phase. In this case, the solid support is a 96-well polystyrene microtiter plate that has a high affinity for proteins. After an appropriate incubation time, the plate was washed with a buffer solution. Solutions of the mercuric ion standards and of samples were then added to each well of the plate. After a brief incubation period, the plate was washed again. An appropriate dilution of the enzyme-labelled second sandwich chelator was then added to each well of the plate. Again, after a brief incubation period, the plate was washed and the appropriate enzyme substrate added to each well of the plate. The enzyme-catalyzed conversion of the substrate into a chromogenic product was allowed to proceed for a short color development period. Finally, the optical absorbance of the liquid in each well was read at the appropriate wavelength with an electronic plate reader. A dose response curve such as the one in FIG. 3 was then generated from the data.

The previously outlined procedure is an example of a sequentially incubated two site assay. It is also possible to conduct this assay with simultaneous incubation of the standards/samples with the second sandwich chelator. The results are similar and obtained faster because one incubation step is eliminated. This format may, however, give less reliable results when the samples have a wide range of analyte concentrations.

Different chelator combinations have been successfully used in both formats to obtain dose response curves. The assay system shown in FIG. 4, employing a sequential incubation format combining coating chelator #142 (protein: OVA) with enzyme linked chelator #153 (enzyme: AP), is one of the assays that has been characterized most extensively. The specific steps involved in the experimental procedure are as follows:

1. Incubation with First Sandwich Chelator

A 1:40 dilution of the first sandwich chelator, #142-OVA was made in 50 mM carbonate buffer at pH 9.6. This solution was then added to the wells of a microtiter plate in volumes of 100 μl per well. The plate was then incubated at 5° C. for 12 to 15 hours to allow the adsorption process to reach equilibrium.

2. Incubation with Standards and Samples

Mercury standards were mixed in 100 mM sodium acetate buffer at pH 5.5 at concentrations ranging from 300.0 to 0.1 nM in 0.5 log serial increments. Unknown samples were diluted at various rates with sodium acetate buffer. As it was pointed out above, the unknown samples must be tested at several distant dilutions to secure that the optical densities fall within the assay's increasing linear range.

After the plate was incubated for the prescribed amount of time with the coating solution, i.e., the first sandwich chelator, it was washed with sodium acetate buffer (5×400 μl/well) and patted dry. 100 μl per well of either mercuric ion standard or sample was added to the plate in quadruplicate form to minimize the effects of well-specific incongruities (FIG. 8). The plate was then incubated for 1 hour at 25° C.

3. Incubation with Second Sandwich Chelator

A 1:40 dilution of the second sandwich chelator, #153-AP was made in sodium acetate buffer containing 0.05% Tween 20 surfactant to reduce the non-specific binding of this chelator to the plate surface or to the first sandwich chelator. The plate which had been incubated for one hour with mercuric ion standards and unknown samples was then washed five times and dried as previously before. This step was followed by the addition of the second sandwich chelator solution to the plate in volumes of 100 μl/well and then by a 1 hour incubation at 25° C.

4. Reaction with the Enzyme Substrate

After a one hour incubation with the second sandwich chelator, i.e., #153AP, the plate was washed five times, then 100 μl/well of the appropriate substrate solution was added. Reporter enzymes used were AP and HRP. The substrate for the HRP tracer consisted of 100 mM acetate buffer at pH 5.5 which contained 0.004% w/v $H_2O_2$ and 0.01% w/v TMB. After about 15 minutes of color development, maximum color contrast is achieved and further color development is stopped by the addition of 50 μl per well of 4M $H_2SO_4$. In the case of AP tracer, a 10% v/v diethanolamine solution containing 0.1% w/v $MgCl_2$ and 0.1% w/v disodium p-nitrophenyl phosphate was used, followed by a 30 to 60 minutes color development period. The TMB product was read at 450 nm while the disodium p-nitrophenyl phosphate product was read at 405 nm.

Table I contains the data regarding the performance of the combination of coating chelator #142-OVA (i.e., the first sandwich chelator) with the enzyme linked chelator #153-AP (i.e., the second sandwich chelator). Remarkably, most of the metal ions investigated did not interfere with the mercury analysis. Although finite level of cross-reactivity with silver (Ag(I)) ion was detected, the assay's sensitivity for this metal is not as high as for $Hg^{2+}$. Moreover, silver would not normally be expected to be an abundant contaminant in most environmental media where the presence of mercury is a concern. Should the interference from silver or other metals become problematic, a proper cleanup procedure (e.g., chelate extraction, ion-exchange chromatography) prior to the mercury analysis may be necessary. Alternatively, the use of masking agents with this system can enhance the target specificity. It is worth noting that neither this assay system nor any other tested combinations of the chelators shown at FIG. 2 exhibited any cross reactivity with methylmercury. This important characteristic of the assay allows the quantification of methylmercury in environmental samples by assessing the difference in response between a sample aliquot which has been completely oxidized with concentrated $HNO_3$ or similar agents and an untreated aliquot of the same sample (organic Hg=total Hg–inorganic Hg). Other mercury species may be ignored in most applications, as is detailed above, because most of the mercury in aqueous environmental samples is either in the form of methylmercury or mercuric (Hg(II)) ions. It will be readily apparent to those of skill in the art that should analysis of other species be important standard techniques can be employed to convert them to Hg(II) for analysis.

TABLE I

Cross-Reactivity Data for the Sequential Incubation Assay System #142-OVA/#153-AP

| Metal Ion | $OD_{50}$ (nM) | Cross-Reactivity (%) |
|---|---|---|
| $Ag^+$ | 211 | 13 |
| $Al^{3+}$ | N/A | — |
| $Ca^{2+}$ | N/A | — |
| $Cd^{2+}$ | N/A | — |
| $Cu^{2+}$ | N/A | — |
| $Fe^{2+}$ | N/A | — |
| $Fe^{3+}$ | N/A | — |
| $Hg^{2+}$ | 28 | 100 |
| $MeHg^+$ | N/A | — |
| $Mg^{2+}$ | N/A | — |
| $Ni^{2+}$ | N/A | — |
| $Pb^{2+}$ | N/A | — |
| $Zn^{2+}$ | N/A | — |

$OD_{50}$: Concentration (nM) of analyte that results in 50% of maximum optical density.
Cross-Reactivity (%) = 100 × $OD_{50}$ of $Hg^{2+}$/$OD_{50}$ of metal ion
N/A: No significant absorbance above background.

F. Experiments Conducted to Optimize the Non-Competitive Assay Conditions

The conditions of the non-competitive assay can be optimized by running routine experiments such as those set forth herein. It will be readily apparent to those of skill in the art that the assay conditions for any chelator-metal combination can be optimized using similar experiments.

1. Coating Buffer

The commonly used coating buffer, 50 mM carbonate buffer at pH 9.6, was chosen because of its documented success in enhancing the adsorption of proteins on polystyrene surfaces. However, as has been stated in the literature, the pH value has only little effect on adsorption and, for instance, it has been found that the use of phosphate buffer at a pH range of 7 to 8 works just as effectively.

2. Wash Buffer 100 mM sodium acetate buffer at pH 5.5 is used both for washing and for incubation with standards/samples and with the second sandwich chelator. Various buffers at 100 mM concentration and also the effect of the pH value of the buffers were tested:

| Buffers | pHs tested |
|---|---|
| HEPES | 7.0, 7.5, 8.0 |
| Bis Tris | 6.0, 6.5, 7.0 |
| Sodium acetate | 4.5, 5.0, 5.5 |

The pH interval for each buffer was chosen on the basis of that specific buffer's effective pH range. It was observed that sodium acetate at pH 5.5 gave the best results in terms of signal to noise ratio. In turn, ionic strengths ranging from 10 mM to 100 mM sodium acetate were then tested. No effect upon assay results was detected from ionic strength variations in this range. 100 mM was arbitrarily chosen for use in the assay to insure maximal buffering capacity when mixed with unknown aqueous samples.

The use of pH 5.5 is a compromise between two opposing unfavorable conditions. It is known from literature reports that under more acidic conditions (pH≦pKa of the dithiocarbamic acid), the decomposition of the chelator thereby releasing carbon disulfide would become significant. In contrast, at too high a pH value, the mercury(II) ion may not remain in solution.

3. Incubation Times

One hour incubation times for both the incubation of coated plates with standards/samples and incubation with enzyme-labelled second sandwich chelator were arbitrarily chosen to allow ample time for chemical equilibrium to be reached.

4. Reagent Concentrations

Simple two dimensional titrations were normally performed to determine the optimal concentration combination of the first and the second sandwich chelator. Quadruplicate samples were run in every case to minimize well-specific plate differences. On one half of the plate wells, 300 nM $Hg^{2+}$ was used while on the other half, zero concentration of $Hg^{2+}$ was used (FIG. 9). The concentration combination of the coating and the enzyme linked chelates that gave the highest optical density contrast was considered to be optimal. Optimal conditions for different batches of coating chelator and reporter chelator preparations ranged from 1:20 to 1:40 for both.

5. Surfactants

A detergent was advantageously used during the incubation with the second sandwich chelator to reduce the incidence of non-specific binding to the solid phase or to the first sandwich chelator. Without the use of a proper surfactant, non-specific binding might results in a high background signal. The detergents investigated at their critical micelle concentrations were:

| Surfactant | Type |
|---|---|
| a. 3-[(3-Cholamidopropyl)-dimethylamino]-1-propane-sulfonate dihydrate | zwitterionic |
| b. Dodecylethyldimethyl-ammonium bromide | cationic |
| c. Sodium dodecyl sulfate | anionic |
| d. Glycodeoxycholic acid | anionic |
| e. Aliquat 336 (tricaprylmethylammonium chloride) | cationic |
| f. n-Dodecyl β-D-Glucopyranoside | non-ionic |
| g. Tween 20 (polyoxyethylene-sorbitan monolaurate) | anionic |

It was found that the use of 0.05% Tween 20 resulted in the lowest background signal.

G. Examples of Performing the Competitive Assay

The system #142-CONA/#196AP is essentially different from the previously described assays; it relies on the competitive inhibition of complex formation between the coating ligand (i.e., the first sandwich chelator) and the mercury attached enzyme by the mercuric ion (See, FIG. 5).

After overnight incubation of #142-CONA onto a 96-well microtiter plate, the plate was washed 4 times with sodium acetate buffer solution. A solution containing #196-AP was added to each well of the plate, followed by an equal volume of standard solutions containing various concentrations of mercuric ion. After one hour of incubation, the plate was washed four times with acetate buffer solution and a solution containing the chromogenic enzyme substrate was added. The resulting color was inversely proportional to the concentration of the inhibiting mercuric ion in the incubation mixture. The specific steps involved in the experimental procedure are as follows:

1. Immobilization of the Chelator

A 1:80 dilution of #142-CONA was made in 50 mM carbonate buffer at pH 9.6. This solution was then added to the wells of a microtiter plate in volumes of 100 μl per well. The plate was then incubated at 5° C. for 12 to 15 hours to allow the adsorption process to reach equilibrium.

2. Incubation with Mercury Linked Tracer and Standards

Mercury standards were prepared in water, previously treated with Chelex 100 ion exchange resin, at concentrations ranging from 6,000 to 0.2 nM in 0.5 log serial increments. A 1:160 dilution of #196-AP was made in 400 mM sodium acetate solution at pH 6.0. Tween 20 was added to bring its final concentration in the solution to 0.10%. The plate which had been incubated overnight with #142-CONA was washed four times with 100 mM sodium acetate solution at pH 5.5. 50 µl of the #196-AP solution were added to each well of the plate, immediately followed by 50 µl per well of the appropriate mercury standards. This simultaneous incubation was allowed to proceed for 1 hour.

3. Reaction with the Enzyme Substrate

After the one hour incubation with #196-AP and standards, the plate was washed four times. 100 µl per well of a 10% diethanolamine solution containing 0.1% w/v $MgCl_2$ and 0.1% w/v disodium p-nitrophenyl phosphate were then added, followed by a 90 minute incubation period. The resulting p-nitrophenol was then read at 405 nm.

Figure 10:
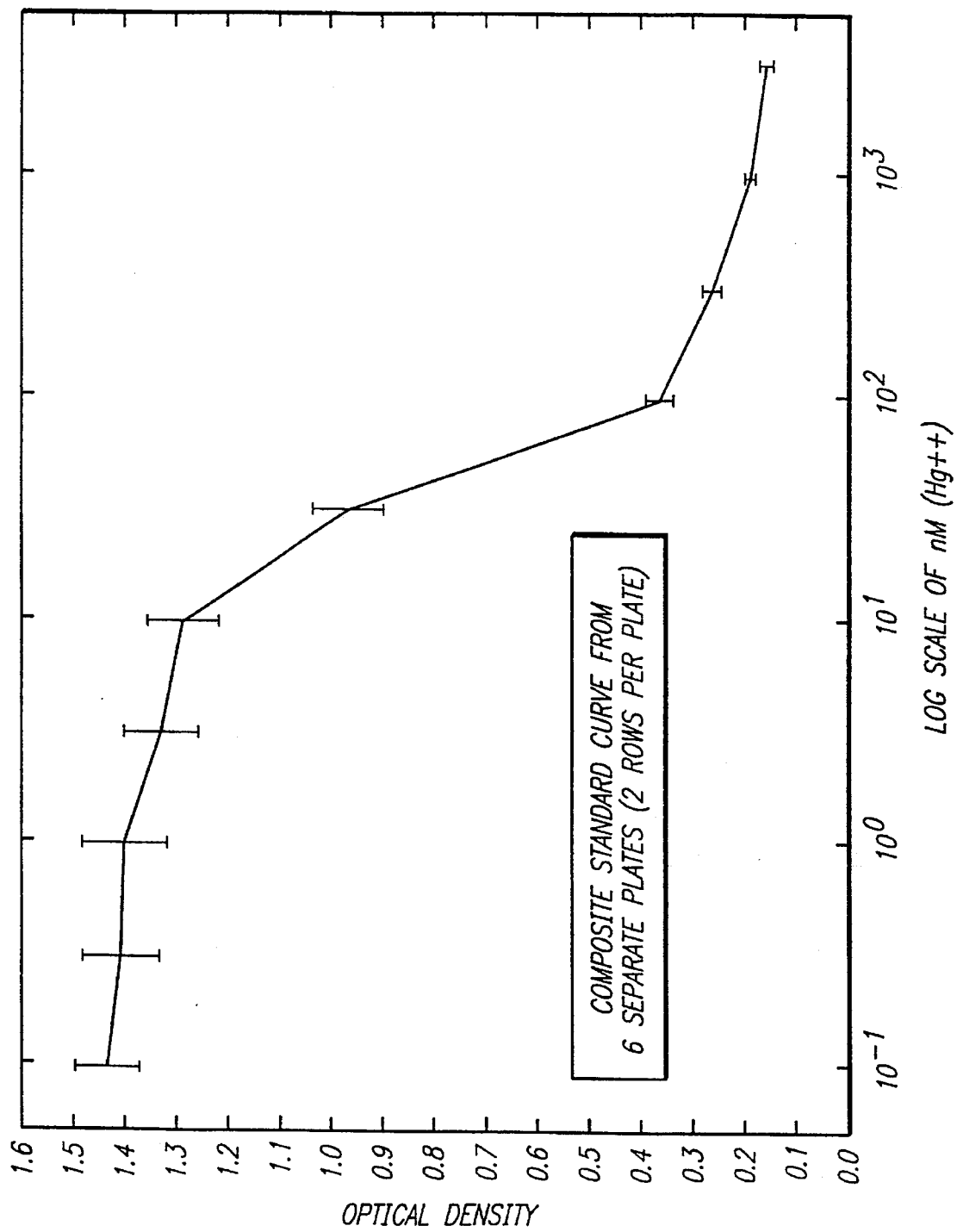
FIG. 10 sets forth the standard curve of the assay system based on the format shown on FIG. 5, supra. Experiments were performed in duplicate rows on six separate plates.

FIG. 10 shows a typical standard curve that can be obtained with the optimized #142-CONA/#196-AP system. The $OD_{50}$ is about 8 ppb (40 nM), the detection limit is about 600 ppt of mercuric ion. The graph is a composite of standard curves (run in duplicate rows) from 6 separate plates. The vertical error bars indicate that variability is higher at lower concentrations of mercuric ions.

H. Experiments Conducted to Optimize Assay Conditions

In order to optimize the overall performance of the assay, the effects of pH, chloride ions, ionic strength of the assay buffer, and some surfactants were investigated. It will be readily apparent to those of skill in the art that the assay conditions for any chelator-metal combination can be optimized using similar experiments.

1. pH Effect

Figure 11:
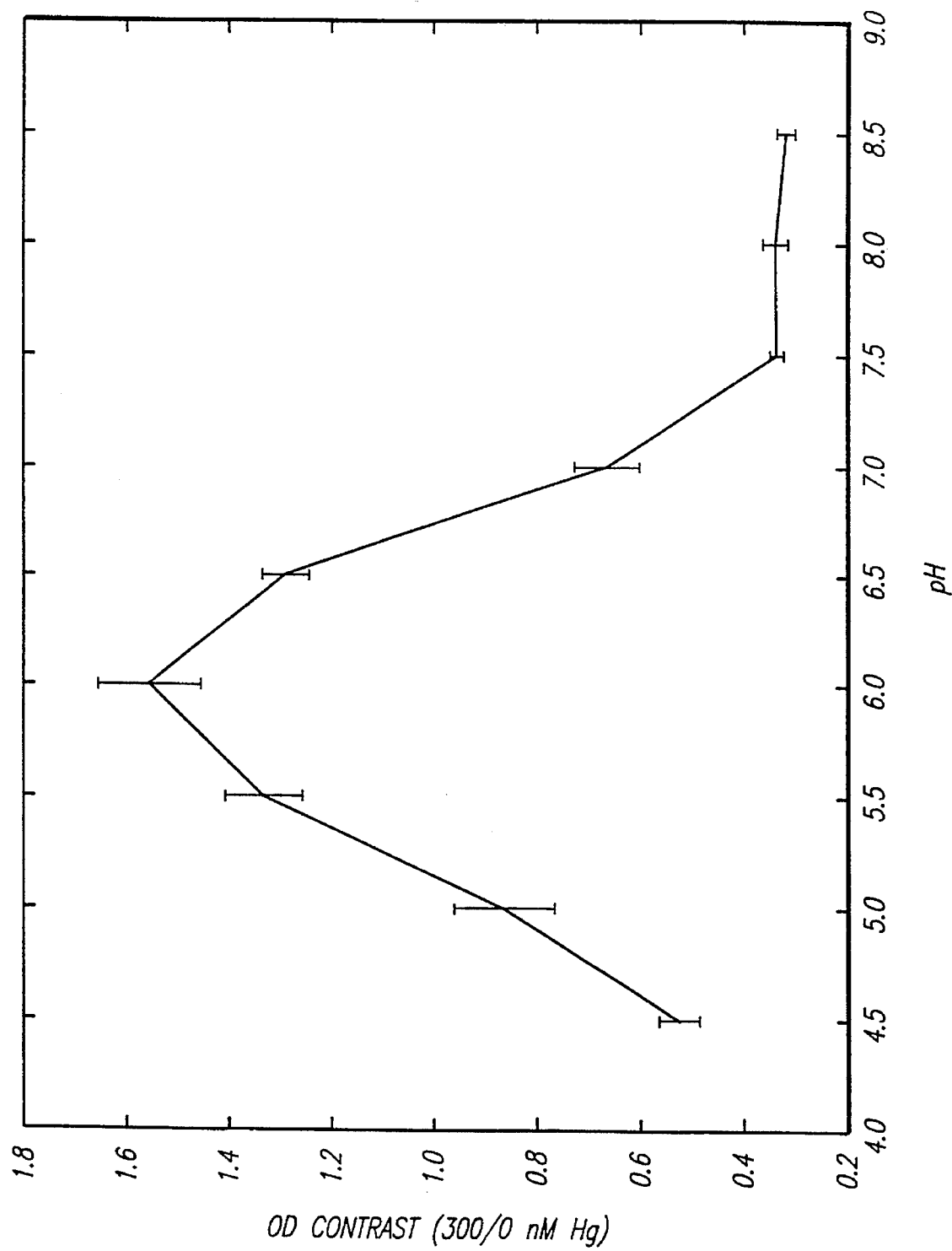
FIG. 11 depicts the pH dependence of system #142-CONA/#196-AP.

To test the effects of pH, 100 mM sodium acetate solutions were made up and aliquoted into 9 volumes. Each of these buffers were then treated by Chelex 100 resin (5 g per 100 ml buffer) overnight to remove traces of interfering metal ions. The pH value of each of the aliquots was adjusted to a value ranging from 4.5 to 8.5. To each one of these, #196-AP and Tween 20 were added. These solutions (50 µl per well) were then added to the plate, followed by the appropriate mercuric ion standards (50 µl per well). The final dilution of #196-AP (in the 100 µl per well volumes) was 1:160 while the final concentration of Tween 20 was 0.05%. The plates were washed with 100 mM sodium acetate buffer (pH 5.5). The pH 6.0 value gave the highest optical density contrast between 300 and 0 nM mercuric ion concentrations (See, FIG. 11).

2. Chloride Effect

Figure 12:
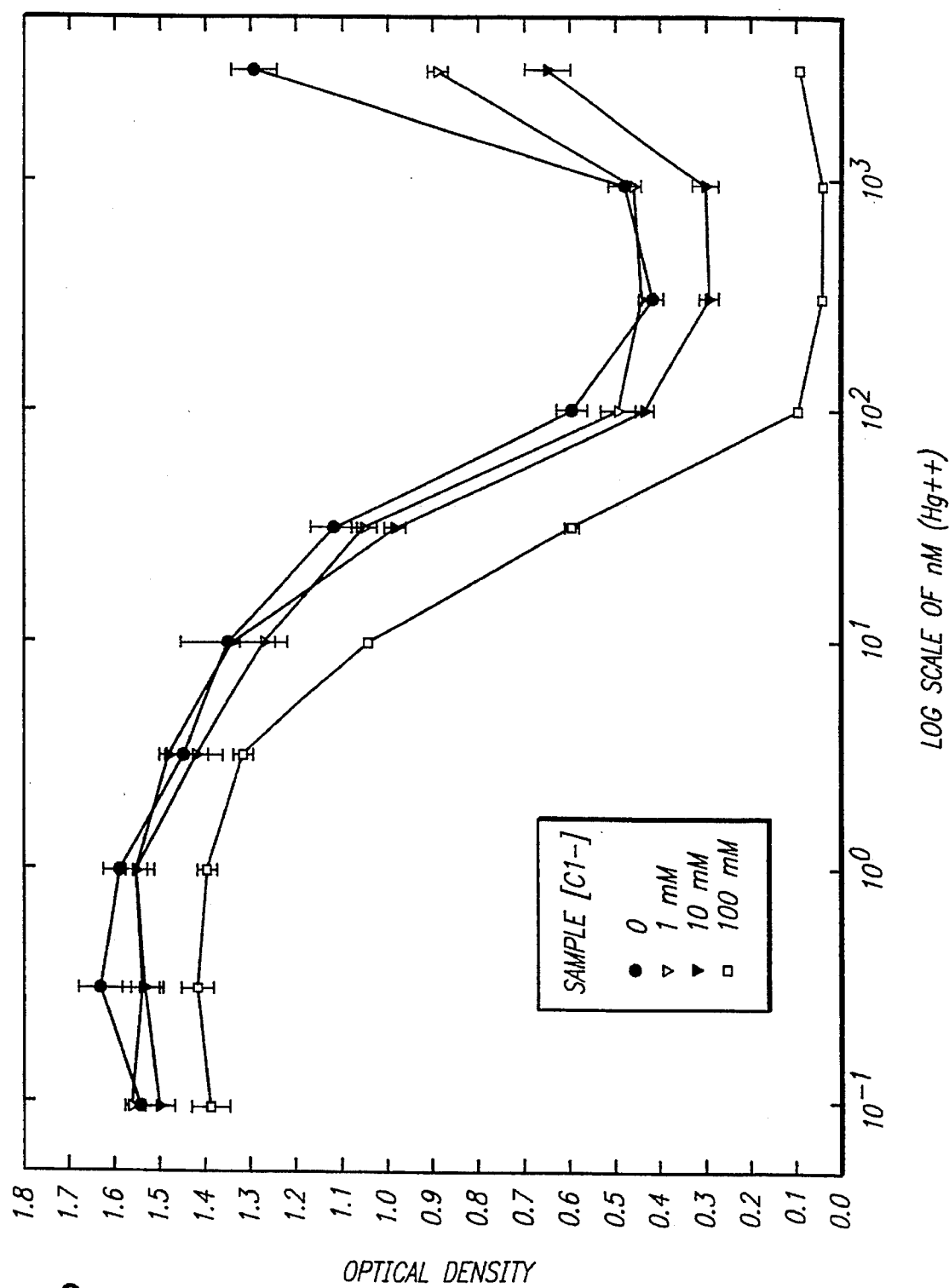
FIG. 12 depicts the effect of chloride ion on system #142-CONA/#196-AP.

A 1M sodium chloride stock solution and water were purified with Chelex 100 resin, and then employed to prepare 1 mM, 10 mM, and 100 mM sodium chloride solutions. These three dilutions along with purified water were used to make mercuric ion standards. These standards were simultaneously incubated with #196-AP for one hour, followed by washing and the addition of substrate. For the purpose of the simultaneous incubation, pH 6.0 sodium acetate buffer was used while pH 5.5 was employed for washing. The presence of chloride ions canceled the increase of optical density at very high mercuric ion concentrations (>1000 nM) observed in the absence of chloride ions (See, FIG. 12).

3. Ionic Strength Effect

Figure 13:
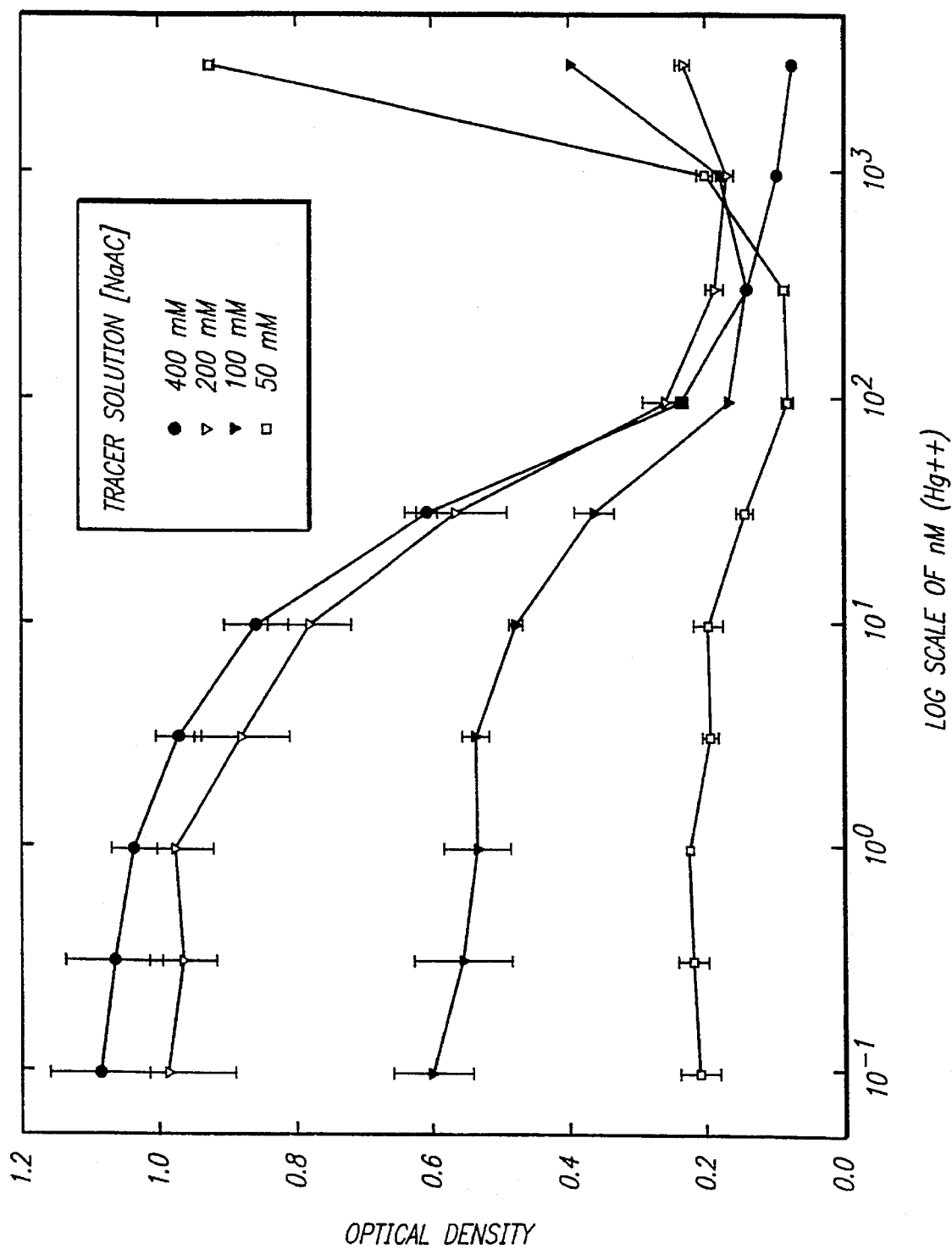
FIG. 13 depicts the effect of ionic strength of the acetate buffer on system #142-CONA/#196-AP.

The results of the previous experiment suggested that ionic strength is an important parameter of the assay. To test the effect of ionic strength of the acetate buffer used in the incubation step, #196-AP tracer was diluted with four separate sodium acetate buffer solutions at 50, 100, 200, and 400 mM at pH 6.0. The resulting solutions were then applied in simultaneous incubations with the mercuric ion dilutions in water. After the 1 hour incubation period, the plate was washed and substrate solution was added. FIG. 13 demonstrates that higher acetate buffer concentrations improved the standard curve by eliminating the upward optical density trend at high mercuric ion concentrations as well as by resulting in better optical density contrasts.

4. Surfactant Effects

Figure 14A:
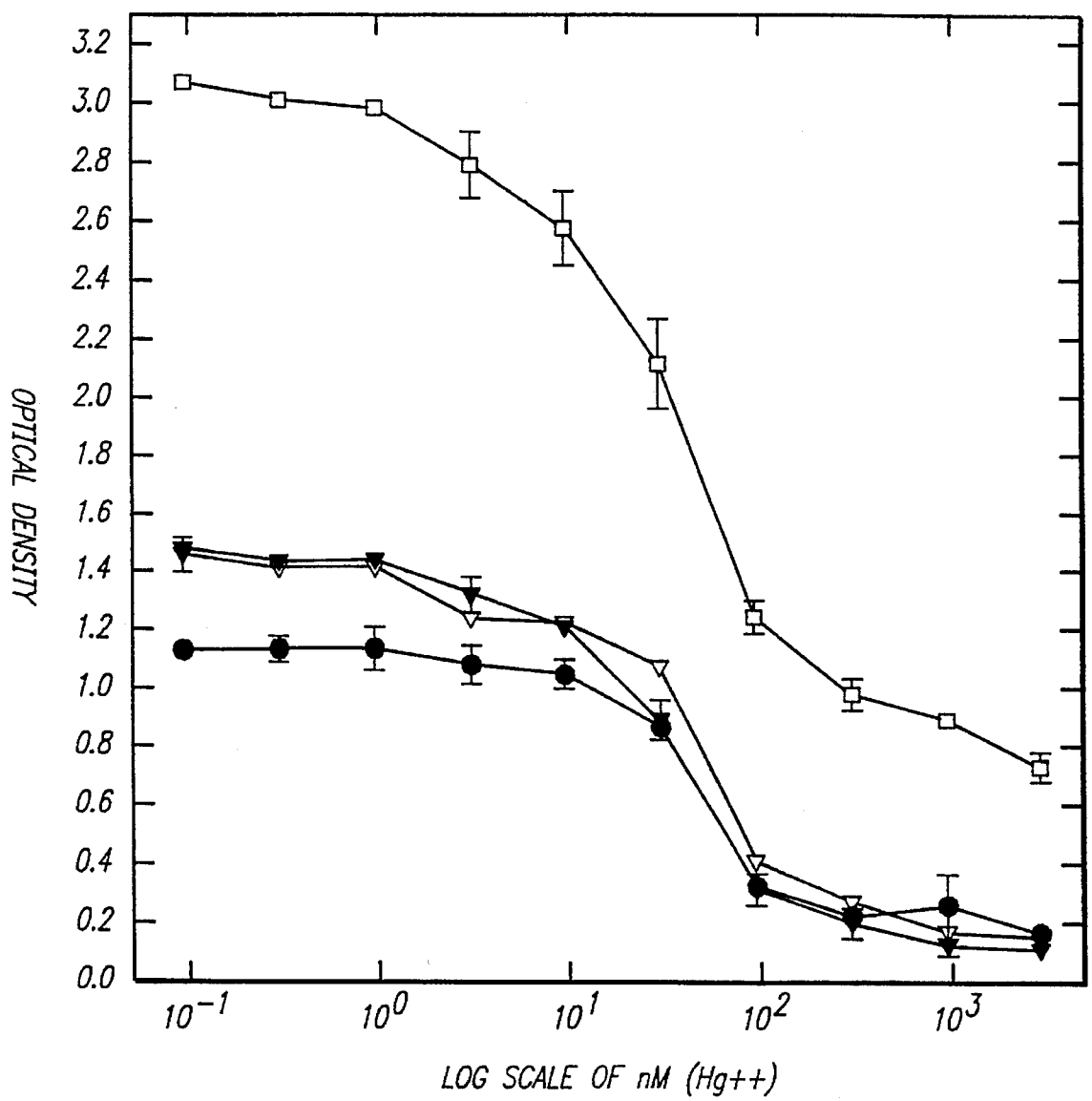
FIG. 14 depicts the effect of surfactants on system #142-CONA/#196-AP.
Figure 14B:
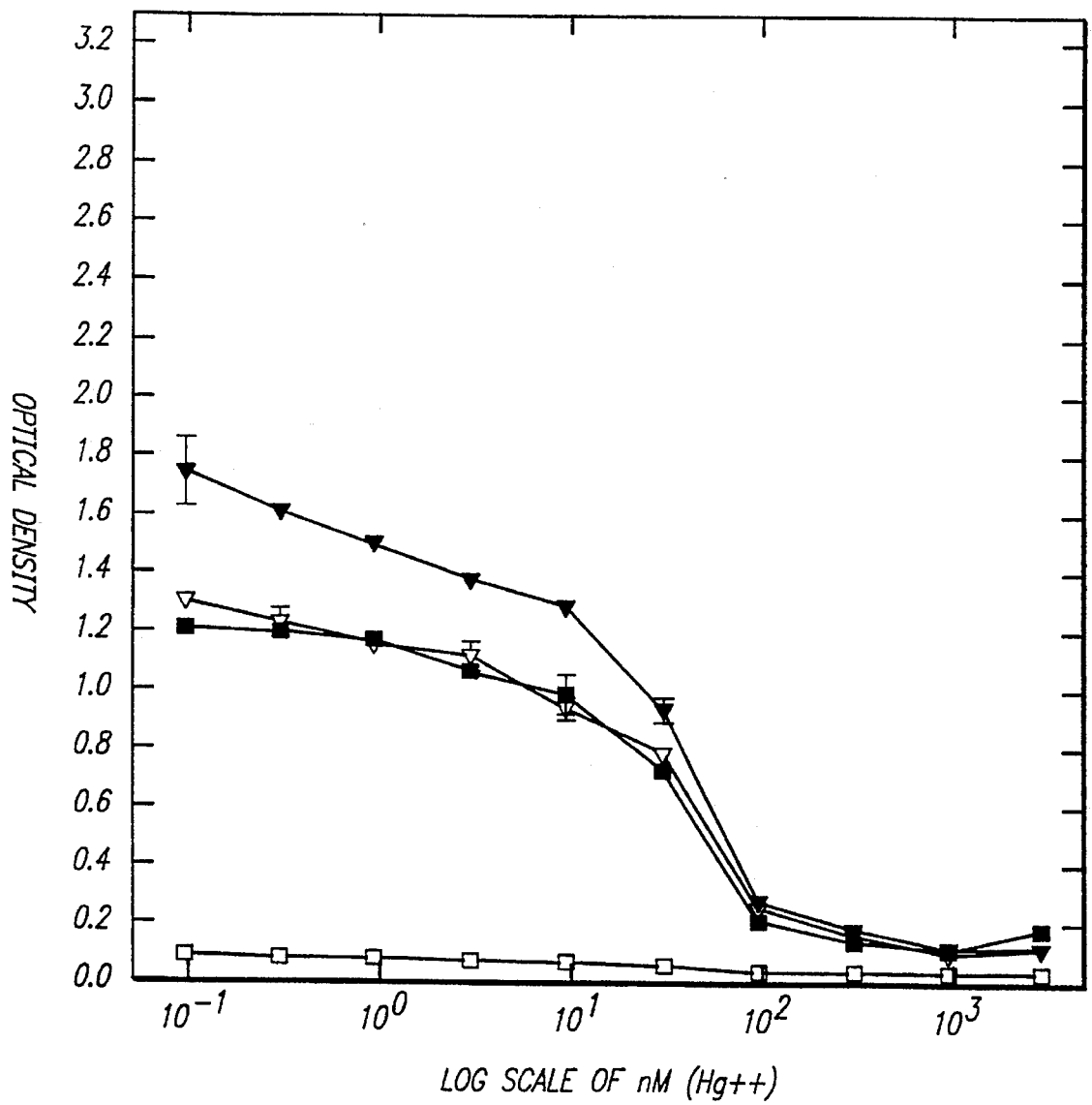

In addition to three concentrations of Tween 20, four other surfactants were tested at their critical micelle concentrations (FIG. 14). #196-AP tracer solutions were prepared in 400 mM acetate buffer (pH 6.0) containing various amounts of surfactants. The surfactants and their well concentrations were 0.025%, 0.050%, and 0.100% of Tween 20, 14 mM of dodecylethyldimethylammonium bromide (DEDMAB), 8 mM of 3-[(3-cholamidopropyl)-dimethylammonio]-1-propane-sulfonate dihydrate (CHAPS), 8.27 mM of sodium dodecyl sulfate (SDS), and 2 mM of glycodeoxycholic acid (GDCA). The highest optical densities were achieved with the use of DEDMAB. However, high blank values for the this surfactant indicate that it causes non-specific binding of the tracer to the bare plate surface. SDS largely inhibited the binding of the tracer to the immobilized ligand while CHAPS resulted in slightly higher optical density at low mercuric ion concentrations than 0.050% Tween 20. There was no significant improvement made by increasing the concentration of Tween 20 from 0.050% to 0.100%.

From the data obtained during the optimization experiments, it was determined that the competitive assay format should be carried out under the following conditions:

1. Wash with 100 mM sodium acetate at pH 5.5,
2. Use 400 mM sodium acetate at pH 6.0 for dilution of #196-AP,
3. Use a 0.10% concentration of Tween 20 in the tracer solution (diluted finally to 0.05% well concentration by the addition of the standard solution).

I. Cross-Reactivity with other Metal Ions

Figure 15:
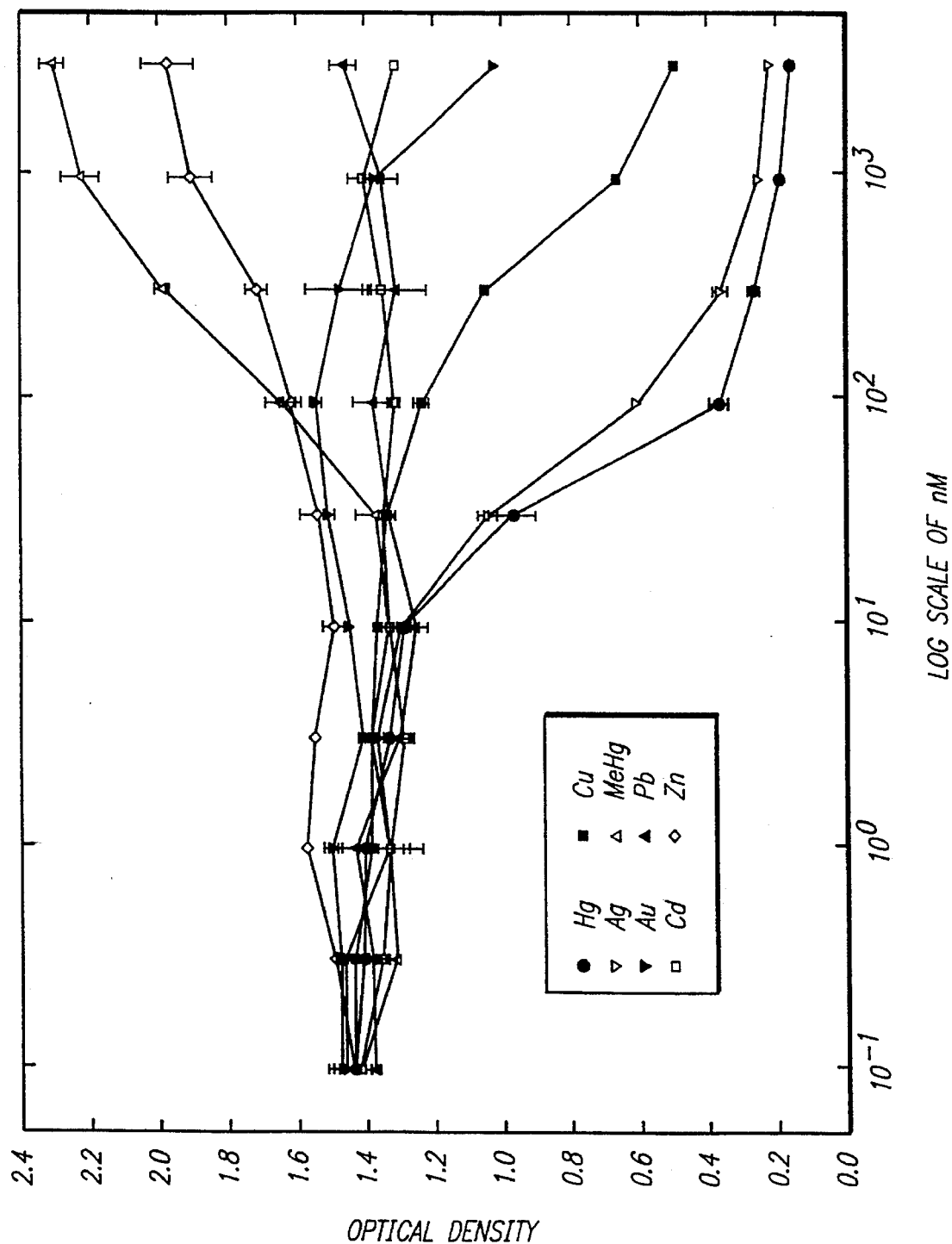
FIG. 15 depicts cross-reactivity investigations with system #142-CONA/#196-AP.

The metal compounds with which the system was tested are listed in Table II. Little or no cross-reactivity (CR) was detected with: $Al^{3+}$, $Cd^{2+}$, $Cr^{3+}$, $Cr^{6+}$, $Co^{2+}$, $Fe^{2+}$, $Fe^{3+}$, $Mg^{2+}$, $Mn^{2+}$, $Ni^{2+}$, $Pb^{2+}$, $Pd^{2+}$, $Pt^{2+}$ (See, FIG. 15). The following metals gave moderate responses: $Au^{3+}$ (CR: <1%), $Cu^{2+}$ (CR: 10%). High cross-reactivity was encountered only with $Ag^+$ (CR: 82%). Unexpected responses, i.e., higher optical densities with increasing metal concentrations, were found with $MeHg^+$ and $Zn^{2+}$. This upward trend, however, was not observed when different assay protocol (e.g., lower buffer concentration) was applied. Although finite level of cross-reactivity with silver (Ag(I)) ion was detected, the assay's sensitivity for this metal is not as high as for $Hg^{2+}$. Moreover, silver would not normally be expected to be an abundant contaminant in most environmental media where the presence of mercury is a concern. Should the interference from silver or other metals become problematic, a proper cleanup procedure (e.g., chelate extraction, ion-exchange chromatography) prior to the mercury analysis may be necessary.

TABLE II

| List of Metal Compounds Used for Cross-Reactivity Studies | | |
| --- | --- | --- |
| Metal Ion | Metal Compound | Vendor |
| $Ag^+$ | $AgNO_3$ | Mallinckrodt Chemical Works |

TABLE II-continued

List of Metal Compounds Used for Cross-Reactivity Studies

| Metal Ion | Metal Compound | Vendor |
| --- | --- | --- |
| $Al^{3+}$ | $Al(NO_3)_3$ | Fisher Scientific |
| $Au^{3+}$ | $AuCl_3$ | Aldrich |
| $Ca^{2+}$ | $CaCl_2.H_2O$ | Mallinckrodt Chemical Works |
| $Cd^{2+}$ | $CdCl_2$ | Aldrich |
| $Co^{2+}$ | $CoCl_2.6H_2O$ | Aldrich |
| $Cr^{3+}$ | $Cr(NO_3)_3.9H_2O$ | Fischer Scientific |
| $Cr^{6+}$ | $Na_2Cr_2O_7.9H_2O$ | Aldrich |
| $Cu^{2+}$ | $CuSO_4.5H_2O$ | Fisher Scientific |
| $Fe^{2+}$ | $FeSO_4.7H_2O$ | Fisher Scientific |
| $Fe^{3+}$ | $FeCl_3.6H_2O$ | Fisher Scientific |
| $Hg^{2+}$ | $Hg(NO_3)_2.H_2O$ | Fisher Scientific |
| $MeHg^+$ | $MeHgOH$ | Alfa |
| $Mg^{2+}$ | $MgCl_2$ | Aldrich |
| $Mn^{2+}$ | $Mn(CH_3CO_2)_2.4H_2O$ | Aldrich |
| $Ni^{2+}$ | $Ni(CH_3CO_2)_2.4H_2O$ | Aldrich |
| $Pb^{2+}$ | $Pb(NO_3)_2$ | Aldrich |
| $Pd^{2+}$ | $Pd(CH_3CO_2)_2$ | Aldrich |
| $Pt^{2+}$ | $PtCl_2$ | Alfa |
| $Zn^{2+}$ | $ZnCl_2$ | Baker |

All of the publications and references mentioned herein above are incorporated in their entirety by reference. Moreover, the foregoing is offered primarily for purposes of illustration. It will be readily apparent to those skilled in the art that the operating conditions, materials, procedural steps and other parameters of the methods described herein may be further modified or substituted in various ways without departing from the spirit and scope of the invention.

What is claimed is:

1. A method for assaying for the presence of a metal ion in a sample suspected of containing said metal ion, said method comprising:

(a) contacting said sample with a solid support, said solid support having a first sandwich chelator immobilized thereon in a manner such that said first sandwich chelator is capable of binding with said metal ion to form a chelate complex;

(b) contacting said sample with a second sandwich chelator, said second sandwich chelator having a reporter moiety molecule or atom immobilized thereon in a manner such that said second sandwich chelator is capable of binding with said chelate complex to form a sandwich chelate complex; and (c) detecting the presence of said sandwich chelate complex and, in turn, said metal ion through the presence or absence of said reporter.

2. A method in accordance with claim 1 wherein said metal ion is selected from the group consisting of antimony, arsenic, beryllium, cadmium, cerium, chromium, cobalt, copper (Cu(II)), gold, lead, manganese, mercury (Hg (II)), nickel, palladium, selenium, silver, thallium, uranium, zinc and zirconium.

3. A method in accordance with claim 2 wherein said metal ion is mercury (Hg (II)).

4. A method in accordance with claim 1 wherein said solid support is selected from the group consisting of cellulose, agarose, dextran, polyacrylate, polyacrylamide, polystyrene and their derivatives.

5. A method in accordance with claim 1 wherein said first and said second sandwich chelators are selected from the group consisting of dithiocarbamates, 2,3-dimercaptopropanesulphonic acid, 2,3-dimercaptopropanol-1, D,L-penicillamine, 2-(3-sulfobenzoyl)pyridine-2-pyridylhydrazone, selenohydryl-containing compounds, 4-(2-pyridylazo)resorcinol, diphenylthiocarbazone, 1-(2-pyridylazo)-2-naphthol, 6-amino-1-naphthol-3-sulphonic acid, histidine and acetylacetone.

6. A method in accordance with claim 5 wherein said first and said second sandwich chelators are dithiocarbamates.

7. A method in accordance with claim 1 wherein said first sandwich chelator is immobilized on said solid support through a linker molecule selected from the group consisting of proteins, carbohydrates, lipids, peptides, nucleic acids and synthetic polymers.

8. A method in accordance with claim 7 wherein said linker molecule is a protein selected from the group consisting of bovine serum albumin, conalbumin, keyhole limpet hemocyanin and ovalbumin.

9. A method in accordance with claim 1 wherein said reporter is selected from the group consisting of enzymes, chromogens, fluorophores, radioisotopes and biotin.

10. A method in accordance with claim 9 wherein said reporter is an enzyme selected from the group consisting of horseradish peroxidase and alkaline phosphatase.

11. A method in accordance with claim 1 further comprising the step of quantitating the amount of said metal ion present in said sample.

12. A kit for assaying for the presence of a metal ion in a sample suspected of containing said metal ion, said kit comprising:

a solid support having a first sandwich chelator immobilized thereon in a manner such that said first sandwich chelator is capable of binding with said metal ion to form a chelate complex; and a second sandwich chelator, said second sandwich chelator having a reporter moiety molecule or atom immobilized thereon in a manner such that said second sandwich chelator is capable of binding with said chelate complex to form a sandwich chelate complex.

13. A kit in accordance with claim 12 wherein said metal ion is selected from the group consisting of antimony, arsenic, beryllium, cadmium, cerium, chromium, cobalt, copper (Cu(II)), gold, lead, manganese, mercury (Hg (II)), nickel, palladium, selenium, silver, thallium, uranium, zinc and zirconium.

14. A kit in accordance with claim 12 wherein said solid support is selected from the group consisting of cellulose, agarose, dextran, polyacrylate, polyacrylamide, polystyrene polyvinyl chloride and their derivatives.

15. A kit in accordance with claim 12 wherein said first and said second sandwich chelators are selected from the group consisting of dithiocarbamates, 2,3-dimercaptopropanesulphonic acid, 2,3-dimercaptopropanol-1, D,L-penicillamine, 2-(3-sulfobenzoyl)pyridine-2-pyridylhydrazone, selenohydryl-containing compounds, 4-(2-pyridylazo)resorcinol, diphenylthiocarbazone, 1-(2-pyridylazo)-2-naphthol, 6-amino-1-naphthol-3-sulphonic acid, histidine and acetylacetone.

16. A kit in accordance with claim 12 wherein said first and said second sandwich chelators are dithiocarbamates and said metal ion is mercury (Hg (II)).

17. A kit in accordance with claim 12 wherein said first sandwich chelator is immobilized on said solid support through a linker molecule selected from the group consisting of proteins, carbohydrates, lipids, peptides, nucleic acids and synthetic polymers.

18. A kit in accordance with claim 17 wherein said linker molecule is a protein selected from the group consisting of bovine serum albumin, conalbumin, keyhole limpet hemocyanin and ovalbumin.

19. A kit in accordance with claim 12 wherein said reporter is selected from the group consisting of enzymes, chromogens, fluorophores, radioisotopes and biotin.

20. A kit in accordance with claim 19 wherein said reporter is an enzyme selected from the group consisting of horseradish peroxidase and alkaline phosphatase.

21. A competitive method for assaying for the presence of a metal ion in a sample suspected of containing said metal ion, said method comprising:

(a) contacting said sample with a solid support, said solid support having a chelator immobilized thereon in a manner such that said chelator is capable of binding with said metal ion to form a chelate complex;

(b) adding to said sample an organometallic compound that is capable of binding with said chelator to form a chelate complex, said organometallic compound having immobilized thereon a reporter group; and (c) detecting the presence of said metal ion through the presence or absence of said reporter group.

22. A method in accordance with claim 21 wherein said metal ion is selected from the group consisting of antimony, arsenic, beryllium, cadmium, cerium, chromium, cobalt, copper (Cu(II)), gold, lead, manganese, mercury (Hg (II)), nickel, palladium, selenium, silver, thallium, uranium, zinc and zirconium.

23. A method in accordance with claim 21 wherein said solid support is selected from the group consisting of cellulose, agarose, dextran, polyacrylate, polyacrylamide, polystyrene polyvinyl chloride and their derivatives.

24. A method in accordance with claim 21 wherein said chelator is selected from the group consisting of dithiocarbamates, 2,3-dimercaptopropanesulphonic acid, 2,3-dimercaptopropanol-1, D,L-penicillamine, 2-(3-sulfobenzoyl)pyridine-2 -pyridylhydrazone, selenohydryl-containing compounds, 4-(2-pyridylazo)resorcinol, diphenylthiocarbazone, 1-(2-pyridylazo)-2-naphthol, 6-amino-1-naphthol-3-sulphonic acid, histidine and acetylacetone.

25. A method in accordance with claim 21 wherein said chelator is a dithiocarbamate and said metal ion is mercury (Hg (II)).

26. A method in accordance with claim 21 wherein said chelator is immobilized on said solid support through a linker molecule selected from the group consisting of proteins, carbohydrates, lipids, peptides, nucleic acids and synthetic polymers.

27. A method in accordance with claim 26 wherein said linker molecule is a protein selected from the group consisting of bovine serum albumin, conalbumin, keyhole limpet hemocyanin and ovalbumin.

28. A method in accordance with claim 21 wherein said reporter group is selected from the group consisting of enzymes, chromogens, fluorophores, radioisotopes and biotin.

29. A method in accordance with claim 28 wherein said reporter group is an enzyme selected from the group consisting of horseradish peroxidase and alkaline phosphatase.

30. A method in accordance with claim 21 wherein said organometallic compound is a organomercuric compound.

31. A method in accordance with claim 21 further comprising the step of quantitating the amount of said metal ion present in said sample.

* * * * *